US011891459B2

(12) United States Patent
Berezina et al.

(10) Patent No.: US 11,891,459 B2
(45) Date of Patent: Feb. 6, 2024

(54) CHITIN, HYDROLYSATE AND METHOD FOR THE PRODUCTION OF ONE OR MORE DESIRED PRODUCTS FROM INSECTS BY MEANS OF ENZYMATIC HYDROLYSIS

(71) Applicant: YNSECT, Evry (FR)

(72) Inventors: Nathalie Berezina, Paris (FR); Antoine Hubert, Alfortville (FR); Fabrice Berro, Paris (FR); Jean-Gabriel Levon, Paris (FR); Karine Le Roux, Milly la Foret (FR); Cecilia Socolsky, Paris (FR); Lorena Sanchez, Juvisy (FR); Sophie Laurent, Paris (FR)

(73) Assignee: YNSECT

( * ) Notice: Subject to any disclaimer, the term of this patent is extended or adjusted under 35 U.S.C. 154(b) by 190 days.

(21) Appl. No.: 15/541,186

(22) PCT Filed: Dec. 30, 2015

(86) PCT No.: PCT/FR2015/053781
§ 371 (c)(1),
(2) Date: Jun. 30, 2017

(87) PCT Pub. No.: WO2016/108033
PCT Pub. Date: Jul. 7, 2016

(65) Prior Publication Data
US 2018/0016357 A1 Jan. 18, 2018

(30) Foreign Application Priority Data
Dec. 31, 2014 (FR) ........................ 1463512

(51) Int. Cl.
C08B 37/08 (2006.01)
C12P 19/26 (2006.01)
C08B 37/00 (2006.01)
C08L 5/08 (2006.01)
C12P 21/06 (2006.01)
C07K 14/435 (2006.01)

(52) U.S. Cl.
CPC ...... C08B 37/003 (2013.01); C07K 14/43563 (2013.01); C08B 37/0003 (2013.01); C08L 5/08 (2013.01); C12P 19/26 (2013.01); C12P 21/06 (2013.01)

(58) Field of Classification Search
CPC ... C08B 37/003; C08B 37/0003; C12P 21/06; C12P 19/26; C07K 14/43563; C08L 5/08
See application file for complete search history.

(56) References Cited

U.S. PATENT DOCUMENTS

| | | | |
|---|---|---|---|
| 4,958,011 A | 9/1990 | Bade | |
| 6,326,165 B1* | 12/2001 | Wilson | C07K 14/43563 435/252.3 |
| 10,995,124 B2* | 5/2021 | Berezina | C07K 14/43563 |
| 2003/0233982 A1 | 12/2003 | Zhang | |
| 2008/0075818 A1 | 3/2008 | Papadoyianis et al. | |
| 2014/0100361 A1* | 4/2014 | Le Roux | C12P 19/04 536/20 |
| 2015/0132433 A1* | 5/2015 | Dossey | A23L 3/40 426/2 |

FOREIGN PATENT DOCUMENTS

| | | |
|---|---|---|
| CN | 1297691 | 6/2001 |
| CN | 1415757 | 5/2003 |
| CN | 1415757 A | 5/2003 |
| CN | 101078023 | 11/2007 |
| CN | 101144097 | 3/2008 |
| CN | 101775085 | 7/2010 |
| CN | 101880591 | 11/2010 |
| CN | 101144097 | 12/2010 |
| CN | 102048020 | 5/2011 |
| CN | 102199228 | 9/2011 |
| CN | 102342394 | 2/2012 |
| CN | 102558387 | 7/2012 |
| CN | 102558387 A * | 7/2012 |
| CN | 102578361 | 7/2012 |
| CN | 102816808 | 12/2012 |
| CN | 102993334 | 3/2013 |
| CN | 103725742 | 4/2014 |
| CN | 103725742 A | 4/2014 |
| CN | 104059953 | 9/2014 |
| FR | 2927336 | 8/2009 |
| FR | 2975706 | 11/2012 |
| JP | H03139291 | 6/1991 |
| JP | 2008212025 A | 9/2008 |
| JP | 2009254348 | 11/2009 |
| JP | 2011-511783 | 4/2011 |

(Continued)

OTHER PUBLICATIONS

CN 102558387 Machine Translation. Jul. 2012. (Year: 2012).*
Barrett, AJ et al. Type and families of endopeptidases. Biochem. Soc. Trans. Aug. 1991. 19(3): 707-715. (Year: 1991).*
Tajik, H et al. Preparation of chitosan from brine shrimp (*Artemia urmiana*) cyst shells and effects of different chemical processing sequences on the physicochemical and functional properties of the product. Molecules. 2008. 13: 1263-1274. (Year: 2008).*
Wu (CN 101078023) published Nov. 28, 2007. Machine Translation. (Year: 2007).*
Finke, MD et al. Estimate of chitin in raw whole insects. Zoo Biology. 2007. 26: 105-115. (Year: 2007).*

(Continued)

*Primary Examiner* — David W Berke-Schlessel
*Assistant Examiner* — Susan E. Fernandez
(74) *Attorney, Agent, or Firm* — Panitch Schwarze Belisario & Nadel LLP; Erin M. Dunston

(57) ABSTRACT

The invention relates to chitin, a hydrolysate and a method for the production of at least one desired product from insects. More specifically, the invention relates to a method for the production of at least one desired product from insects, comprising an insect cuticle pressing step, followed by the enzymatic hydrolysis of the insect cuticles using a proteolytic enzyme.

10 Claims, 24 Drawing Sheets

(56) References Cited

FOREIGN PATENT DOCUMENTS

Figure 1:
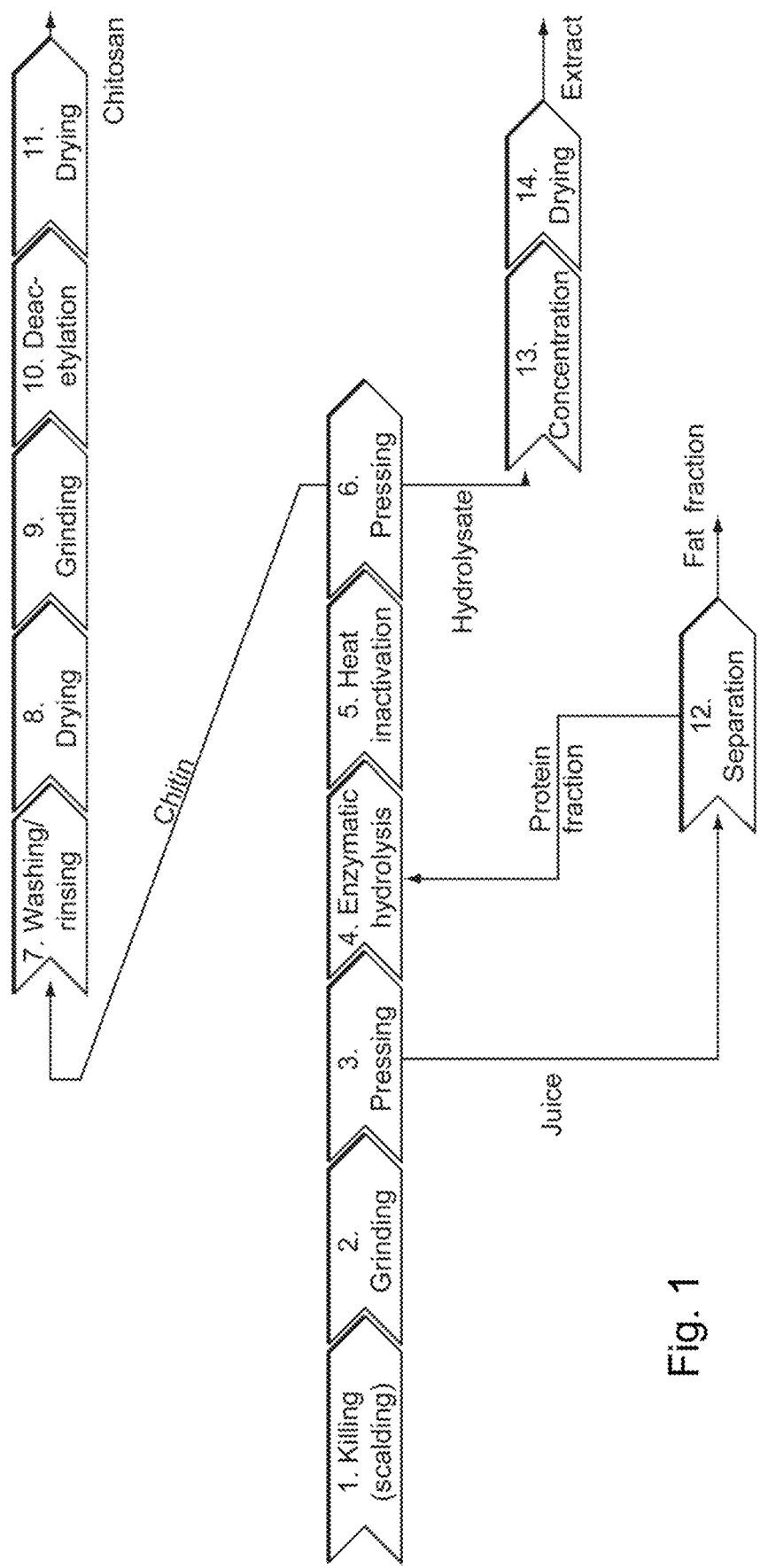

| JP | 2012116773 A | 6/2012 | | |
|---|---|---|---|---|
| JP | 2014-522240 | 9/2014 | | |
| RU | 2345139 | 1/2009 | | |
| WO | WO 2004049818 | 6/2004 | | |
| WO | WO-2012168618 A1 | * 12/2012 | ............... | C12P 19/04 |
| WO | WO 2013/191548 | 12/2013 | | |
| WO | WO-2013191548 A1 | * 12/2013 | ............... | A23D 9/04 |

OTHER PUBLICATIONS

Downer, RG et al. Patterns of lipid distribution and utilisation in insects. Amer. Zool. 1976. 16: 733-745. (Year: 1976).*

Dai et al., *Angiotensin I-converting enzyme (ACE) inhibitory peptide derived from Tenebrio molitor (L.) larva protein hydrolysate*, 236 Eur Food Res Technol 681-689 (2013).

Nwe et al., *Chitin and Chitosan from Terrestrial Organisms*, Chitin and Chitosan and Their Derivatives Biological Activities and Applications 3-10 (2010).

Wang et al., *Housefly larvae hydrolysate: orthogonal optimization of hydrolysis, antioxidant activity, amino acid compositions and functional properties*, 6 BMC Research 1-10 (2013).

Becker, *Technologies for processing insect-based food ingredients*, Food Technology, DTI, Insect Conference (Nov. 13, 2014).

Bukkens, *The Nutritional Value of Edible Insects*, 36 Ecology of Food and Nutrition 287-319 (1997).

Dreyer et al., *On the Nutritive Value of Mopanie Worms*, 78 South African Journal of Science 33-35 (Jan. 1982).

Eggers, *High Pressure Extraction of Oil Seed*, 62(8) JAOCS 1222-1223 (Aug. 1985).

Gutierrez et al., *Análisis Composicional, Microbiológico y Digestibilidad de la Proteina de la Harina de Larvas de Hermetia Illuscens L (Diptera:Stratiomyiidae) en Angelópolis-Antioquia, Colombia*, 57(2) Rev. Fac. Nac. Agron. Medellín 2491-2499 (2004) (English abstract provided).

Iñiguez-Covarrubias et al., *Biodegradation of Swine Waste by House-Fly Larvae and Evaluation of Their Protein Quality in Rats*, 6(1) Journal of Applied Animal Research 65-74 (1994).

Kroeckel et al., *When a turbot catches a fly: Evaluation of a pre-pupae meal of the Black Soldier Fly (Hermetia illucens) as fish meal substitute—Growth performance and chitin degradation in juvenile turbot (Psetta maxima)*, 364-365 Aquaculture 345-352 (2012).

Özçimen et al., *Production and characterization of bio-oil and biochar from rapeseed cake*, 29 Renewable Energy 779-787 (2004).

Pretorius, *The Evaluation Of Larvae Of Musca domestica (Common House Fly) As Protein Source For Broiler Production*, Master Thesis, Stellenbosch University (entire thesis) (Mar. 2011).

Ramos-Elorduy et al., *Digestibilidad in vitro de Algunos Insectos Comestibles en Mexico*, 49 Folia Entomológica Mexicana 141-154 (1981).

Vedlkamp et al., *Insects as sustainable feed ingredient in pig and poultry diets—a feasibility study*, Report 638 Livestock Research Wageningen UR (Oct. 2012).

St-Hilaire et al., *Fish Offal Recycling by the Black Soldier Fly Produces a Foodstuff High in Omega-3 Fatty Acids*, 38(2) Journal of the World Aquaculture Society 309-313 (2007).

Ward, *Papers from the symposium on Extraction Processes presented at the 73rd AOCS Annual Meeting held in Toronto, Canada M 2-6, 1982*, 61(8) JAOCSW 1358-1359 (Aug. 1984).

*Edible insects—Future prospects for food and feed security*, Food and Agriculture Organization of the United Nations, FAO Forestry paper 171 (2013).

Andersen et al., *Phenolic Compounds Released by Mild Acid Hydrolysis from Sclerotized Cuticle: Purification, Structure, and Possible Origin from Cross-Links*, 8 Insect Biochem. 99-104 (1978).

Duan et al., *Influence of Protease Activity on the Preparation of Chitin and Comparison of the Properties of Different Chitin*, 30(11) Modern Food Science and Technology 119-124 (2014).

Zhu et al., *Research and Application of Chitin and Derivatives Thereof*, Zhejiang University Press, ISBN 978-7-308-13586-3 (Nov. 30, 2014) [Note, this appears to be a book of 557 pages that Applicants do not have. If the Examiner is unable to retrieve a copy of the book via USPTO resources and wishes to have additional information, the Examiner is respectfully requested to contact Applicants' attorney].

* cited by examiner

- purity of the chitin
- lipid content in the hydrolysate
- lipid content in the chitin

CHITIN, HYDROLYSATE AND METHOD FOR THE PRODUCTION OF ONE OR MORE DESIRED PRODUCTS FROM INSECTS BY MEANS OF ENZYMATIC HYDROLYSIS

CROSS-REFERENCE TO RELATED APPLICATIONS

This application is a U.S. National Stage Application pursuant to 35 U.S.C. § 371 of International Patent Application PCT/FR2015/053781, filed on Dec. 30, 2015, and published as WO 2016/108033 on Jul. 7, 2016, which claims priority to French Patent Application 1463512, filed on Dec. 31, 2014, all of which are incorporated herein by reference in their entireties for all purposes.

The present invention relates to a method for the production of at least one product of interest from insects. More particularly, the invention relates to a method for the production of chitin and/or chitosan by enzymatic hydrolysis of insect cuticles. It also relates to a specific chitin and a hydrolysate.

According to the invention, by "chitin" is meant any type of chitin derivative, i.e. any type of polysaccharide derivative comprising N-acetylglucosamine units and D-glucosamine units, in particular the chitin-polypeptide copolymers (sometimes referred to as "chitin/polypeptide composite").

Chitin is said to be the second most synthesized polymer in the living world after cellulose. In fact, chitin is synthesized by many species in the living world: it constitutes part of the exoskeleton of crustaceans and insects and the lateral wall which surrounds and protects fungi. More particularly, in insects, chitin thus constitutes 3 to 60% of their exoskeleton.

By "chitosan" is meant, according to the present invention, the products of the deacetylation of chitin. The usual limit between chitosan and chitin is determined by the degree of acetylation: a compound having a degree of acetylation less than 50% is called chitosan, and a compound having a degree of acetylation greater than 50% is called chitin.

Chitin and/or chitosan are used in numerous applications: cosmetic (cosmetic composition), medical and pharmaceutical (pharmaceutical composition, treatment of burns, biomaterials, corneal dressings, suture material), dietetics and food processing, technical (filtering, texturizing, flocculating or adsorbent agents in particular for water filtration and purification), etc. In fact, chitin and/or chitosan are materials that are biocompatible, biodegradable and non-toxic.

Traditionally, chitin is extracted chemically from crustaceans, from cephalopods, but also, more exceptionally, from fungi. The chemical route uses large quantities of reagents (such as hydrochloric acid, sodium hydroxide and bleaching agents), which have the effect of denaturing the structure of chitin such as it exists in the natural state, for example as present in the shell of crustaceans. Moreover, most of the chemical reagents are harmful to humans and the environment and generate large volumes of effluents that have to be treated. Finally, chitin and/or chitosan originating from crustaceans can generate allergic reactions in sensitive persons.

Another route for extraction of chitin is the enzymatic route. This route is considered to be milder, thus making it possible to better preserve the chitin and/or chitosan. However, the chitin obtained by this route is of a brownish colour, requiring purification steps in order to obtain a marketable powder, i.e. of white colour. The existing methods therefore generally comprise one or more steps for removing the impurities from chitin, such as a step of demineralization with acid, carried out prior to enzymatic hydrolysis, and/or a step of bleaching the chitin with an oxidizing agent, carried out after enzymatic hydrolysis. These two steps for the purification of chitin unfortunately have the effect of altering the chemical structure of chitin.

Work undertaken by the inventors demonstrated that it was possible to obtain chitin that is both purer and has a structure closer to the original structure of chitin by carrying out a step of mechanical treatment prior to hydrolysis, namely a step of pressing insect cuticles.

The invention therefore relates to a method for the production of at least one product of interest from insects, comprising the following steps:
(i) pressing insect cuticles, and then
(ii) enzymatic hydrolysis of the insect cuticles with a proteolytic enzyme.

By "product of interest" is meant more particularly chitin and/or chitosan and/or a hydrolysate.

"Hydrolysate" denotes a product that comprises proteins, hydrolysed proteins, peptides, amino acids and/or other compounds derived from a protein, obtainable by enzymatic hydrolysis of proteins.

The product or products of interest are obtained from insects. By "insects" is meant insects at any stage of development, such as an adult, larval or nymph stage. Preferably, the insects used in the method according to the invention are edible.

More particularly, the insects can be selected from the group constituted by the Coleoptera, Diptera, Lepidoptera, Isoptera, Orthoptera, Hymenoptera, Blattoptera, Hemiptera, Heteroptera, Ephemeroptera and Mecoptera, preferably from the Coleoptera, Diptera, Orthoptera and Lepidoptera.

Preferably, the insects are selected from the group constituted by *Tenebrio molitor, Hermetia illucens, Galleria mellonella, Aiphitobius diaperinus, Zophobas morio, Blattera fusca, Tribolium castaneum, Rhynchophorus ferrugineus, Musca domestica, Chrysomya megacephala, Locusta migratoria, Schistocerca gregaria, Acheta domesticus* and *Samia ricini*.

More preferably, the insects are selected from the group constituted by *Tenebrio molitor, Hermetia illucens, Galleria mellonella, Alphitobius diaperinus, Zophobas morio, Blattera fusca, Musca domestica, Chrysomya megacephala, Locusta migratoria, Schistocerca gregaria, Acheta domesticus* and *Samia ricini*, and even more preferably, *T. molitor*.

One or more insect species can be used in the method according to the invention, preferably a single insect species. If several species are used, advantageously two closely related species will be selected, for example *Hermetia illucens* and *Musca domestica*.

The insects are preferably reared, rather than taken from nature. For example, the insects are reared in an insect farm. Breeding the insects in a special farm makes it possible not only to control and eliminate the risks associated with insect-borne diseases, but also to limit the risks associated with the toxicity of food products derived from insects due for example to the presence of insecticides. Moreover, farming makes it possible to control the quality of the supply of insects and limit the costs of supply.

By "insect cuticles" is meant not only the cuticles once they have been separated from the insects, but also the cuticles including some or all of the other constituents of the insect, including the whole insect. In fact, it is possible to apply the method according to the invention to the whole insect, such as ground insects, or only to a part of the insects comprising the cuticles, for example the exuviae and/or the molts of insects, separated naturally and collected by a suitable method.

The cuticle is the outer layer (or exoskeleton) secreted by the epidermis of the insects. Generally it is formed from three layers:
- the epicuticle, which is the thinnest, outermost layer of the cuticle (less than 4 μm); this layer is impermeable to water and comprises a layer of water-repelling wax, as well as a smaller amount of proteins and chitin;
- the exocuticle, which is the intermediate layer of the cuticle; it consists essentially of proteins that have been hardened by tanning, and are responsible for the rigidity of the cuticle; chitin, and optionally melanin; and
- the endocuticle, which is a thin, flexible layer, constituted by a mixture of proteins and chitin.

The main objective of pressing insect cuticles is to remove a fat-rich press juice and/or to enrich the press cake to give a substrate for hydrolysis.

In the method according to the invention, pressing the insect cuticles makes it possible to obtain a press cake comprising an oil (or lipids) content less than or equal to 20%, preferably less than or equal to 15%, more preferably less than or equal to 12%, even more preferably less than or equal to 10%.

In the present application, the ranges of values are understood to be inclusive. Moreover, when "approximately" or "of the order of" precedes a number, this is equivalent to plus or minus 10% of the value of this number.

Likewise, in order to enrich the press cake into a substrate for hydrolysis, pressing the insect cuticles makes it possible to obtain a press cake having a dry matter content comprised between 30% and 60%, preferably comprised between 40% and 55%, and more preferably comprised between 45% and 50%.

Any press system can be used for carrying out the pressing of the insect cuticles, for example a single-screw or twin-screw press (twin-screw press of the Angel type), a filter-press (filter-press of the Choquenet type), a platen press, etc. These systems are well known to a person skilled in the art, who is able to determine the pressing conditions so as to obtain the oil and/or water contents mentioned above.

In the method according to the invention, pressing the insect cuticles is followed by enzymatic hydrolysis.

Preferably, enzymatic hydrolysis is carried out with at least one proteolytic enzyme, preferably a protease. In the present application, the names or suffixes "peptidase" and "protease" are used indiscriminately to denote an enzyme causing lysis of a peptide bond of the proteins. Advantageously, this is carried out for a time of from 4 to 8 h, preferably for 4 to 5 h, at a temperature from 40 to 60° C., preferably 45 to 55° C. and at a pH comprised between 6 and 8, preferably between 6.5 and 7.5.

Enzymatic hydrolysis can be carried out with a single protease or alternatively with a mixture of enzymes containing at least one protease, more preferably a mixture of enzymes containing several proteases, such as a mixture containing an endoprotease and an exoprotease, or a protease and a polysaccharase.

Preferably, the protease is selected from the group constituted by the aminopeptidases, metallocarboxypeptidases, serine endopeptidases, cysteine endopeptidases, aspartic endopeptidases, metalloendopeptidases.

Advantageously, the enzymes can be selected from the following:

| Enzyme(s) | Class | EC number | Supplier | Town | Country |
|---|---|---|---|---|---|
| Flavourzyme | Amino- | EC 3.4.11.1 | Novozyme | Bagsvaerd | Denmark |
| Fungal protease 500 | peptidases | EC 3.4.11.1 | BioCat | Troy | United States |
| Kojizyme | | EC 3.4.11.1 | Novozyme | Bagsvaerd | Denmark |
| Protex P | Serine endopeptidases | EC 3.4.21 | Genencor International B.V. | Leiden | The Netherlands |
| Chymotrypsin | | EC 3.4.21.1 | Novozyme | Bagsvaerd | Denmark |
| Protamex | | EC 3.4.21 | Novozyme | Bagsvaerd | Denmark |
| Elastase | | EC 3.4.21.14 | Novozyme | Bagsvaerd | Denmark |
| Trypsin | | EC 3.4.21.36 | Novozyme | Bagsvaerd | Denmark |
| Alcalase | | EC 3.4.21.4 | Novozyme | Bagsvaerd | Denmark |
| Papain | Cysteine | EC 3.4.22.2 | BioCat | Troy | United States |
| Bromelain (ananase) | endopeptidases | EC 3.4.22.32 | BioCat | Troy | United States |
| Prolyve NP | Aspartic | EC 3.4.23 | Lyven | Colombelles | France |
| Pepsin | endopeptidases | EC 3.4.23.1 | Sigma Aldrich | Saint-Quentin-Fallavier | France |
| Neutral protease | Metallo-endopeptidase | EC 3.4.24.28 | BioCat | Troy | United States |
| Protex 50FP | Endopeptidase | EC 3.4.21 | Genencor International B.V. | Leiden | The Netherlands |
| Pancrealyve | Exo & endo peptidase (cocktail of proteases + amylases) | n.a.* | Lyven | Colombelles | France |
| Izyme BA | Aspartic protease | EC 3.4.23 | Novozyme | Bagsvaerd | Denmark |
| Sumizyme | Enzyme cocktail | n.a.* | Takabio - Shin Nihon | Aichi | Japan |
| Neutrase | Endoprotease Zn base of β amyloliquefaciens | EC 3.4.24 | Novozyme | Bagsvaerd | Denmark |
| Novozyme 37071 | Protease | n.a.* | Novozyme | Bagsvaerd | Denmark |

*n.a.: not applicable

Advantageously, the enzyme used in the hydrolysis is an aspartic endopeptidase, such as Prolyve NP. This type of enzyme makes it possible to obtain very good results in terms of purity of the chitin obtained, especially when this type of enzyme is applied in the hydrolysis of a press cake obtained from Coleoptera and more particularly from *T. molitor*.

The enzyme or the mixture of enzymes is introduced in a quantity ranging from 0.2 to 10% by weight of estimated dry matter, preferably from 0.4 to 8% by weight and more preferably from 0.5 to 2%. By "weight of estimated dry matter" is meant more particularly the weight of dry matter from insects or insect part(s), such as can be estimated when entering the enzymatic hydrolysis step.

In terms of enzymatic activity, the quantity of enzyme or enzyme mixture introduced is equivalent to an activity comprised between 2000 and 5000 SAPU ("Spectrophotometric Acid Protease Unit", described in Example 5 below), preferably between 3000 and 4000 SAPU, per 100 g wet weight, with a water content from 30 to 70%, of substrate to be transformed, i.e. of insect or hydrated insect part(s).

Advantageously, the enzymatic hydrolysis step is carried out in the presence of water, such as fresh water. The quantity of water used in the enzymatic hydrolysis is determined as follows: the ratio of the volume of water in mL to the weight of insect in g is preferably comprised between 0.3 and 10, more preferably between 0.5 and 5, even more preferably between 0.7 and 3, even more preferably of the order of 1. It should be noted that this ratio also corresponds to the ratio of the weight of water to the weight of insect, the density of water being 1.0 g/mL under normal temperature and pressure conditions.

Figure 2:
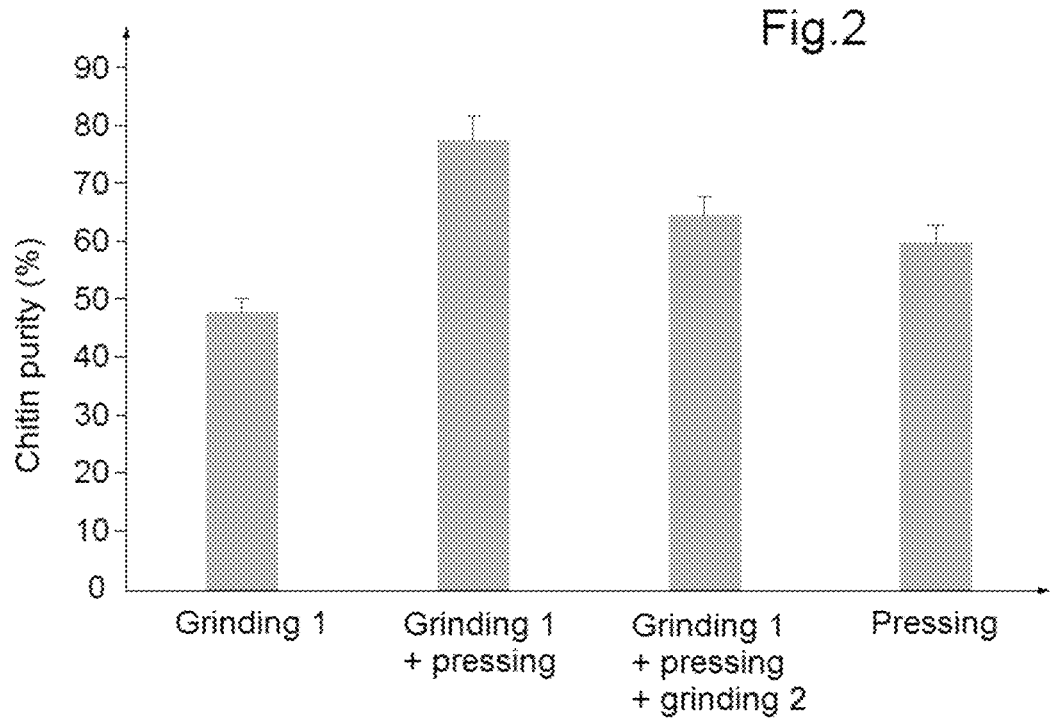

The method according to the invention makes it possible to obtain a chitin having a degree of purity (or gravimetric purity) comprised between 40 and 90%, preferably between 50 and 90%, more preferably comprised between 60 and 85%, and even more preferably of the order of 80% (see Example 2 and FIG. 2).

Moreover, the method according to the invention makes it possible to obtain a hydrolysate having a certain number of advantageous properties, in particular in terms of digestibility, content of lipids and/or proteins, size of protein or amino acid composition.

Preferably, the method according to the invention comprises a grinding step prior to the pressing step.

A particularly preferred embodiment of the invention therefore relates to a method for the production of at least one product of interest from insects, comprising the following steps:
 (i) grinding the cuticles of insects,
 (ii) pressing the cuticles of insects, and then
 (iii) enzymatic hydrolysis of the cuticles of insects with a proteolytic enzyme.

This grinding step has the objective of reducing the cuticles and/or the insects to particles in order to facilitate access of the enzymes to the substrate during enzymatic hydrolysis. This step also makes it possible, when it is followed by a pressing step, to facilitate removal of the press juice and isolation of the solid matter.

Figure 4:
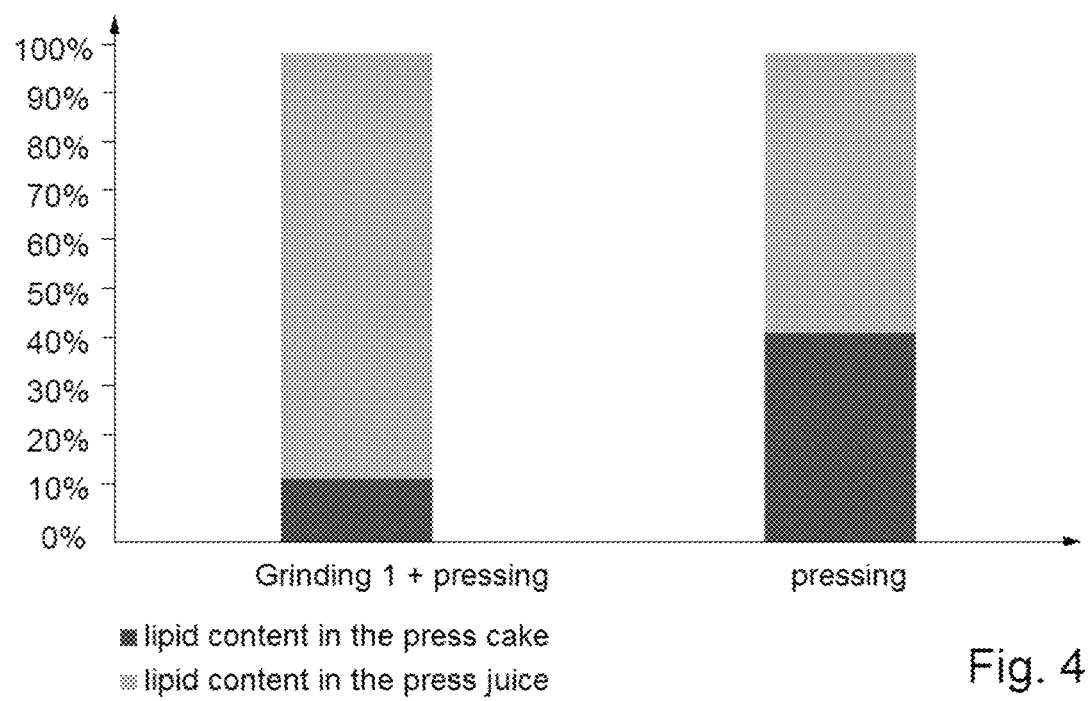

This grinding step also makes it possible to improve the distribution of the lipids originating from the insect between the press cake and the press juice originating from the pressing. In fact, as shown in FIG. 4, the press cake originating from a method comprising both grinding and pressing has a reduced lipid content compared to a press cake from a method comprising only pressing.

More particularly, in the method according to the invention, the grinding and pressing of the insect cuticles makes it possible to obtain a press cake comprising a lipids (or oil) content less than or equal to 15%, preferably less than or equal to 12%, even more preferably less than or equal to 10%.

Grinding can advantageously be carried out with a mixer-grinder, such as a knife mill.

Preferably, at the end of grinding, the size of the particles of insect is less than 1 cm (largest particle size observable using a microscope), preferably less than 0.5 cm, even more preferably a size comprised between 300 µm and 0.5 cm, preferably 500 µm and 0.5 cm and even more preferably between 500 µm and 1 mm.

A quantity of water can be added to facilitate grinding. This quantity of water is determined as follows: the ratio of the volume of water in mL to the weight of insect in g is preferably comprised between 0.3 and 10, more preferably between 0.5 and 5, even more preferably between 0.7 and 3, even more preferably of the order of 1.

Advantageously, the method according to the invention also comprises a step of killing the insects prior to the pressing and/or grinding step.

This killing step can be carried out by conventional methods in the farming of cold-blooded animals and/or animals of small size (crustaceans, fish, snails, etc.), such as cold (freezing), heat (scalding), oxygen deprivation, etc. Advantageously, the insect killing step is carried out by scalding. Scalding not only kills the insects, but also lowers the microbial load (reducing the risk of deterioration and health risk) and inactivates the internal enzymes of the insects which can trigger autolysis, and thus a rapid browning thereof. This scalding is carried out in such a way as to cause death as quickly as possible, in order to respect animal welfare, and according to scientific recommendations.

Alternatively, killing can be carried out by blanching. Blanching has the same advantages as scalding as mentioned above.

Advantageously, the insects are killed, for example by scalding or blanching, and then ground before being pressed.

Preferably, the scalding step is carried out in water, such as fresh water, at a temperature from 95 to 105° C., preferably of the order of 100° C. and for a time from 2 to 20 min, preferably 5 to 15 min.

The quantity of water introduced in this scalding step is determined as follows: the ratio of the volume of water in mL to the weight of insect in g is preferably comprised between 0.3 and 10, more preferably between 0.5 and 5, even more preferably between 0.7 and 3, even more preferably of the order of 1.

Alternatively, the blanching step is carried out with steam and/or with water at a temperature comprised between 80° C. and 130° C., preferably between 90° C. and 120° C.

The method according to the invention can further comprise a step of treatment of the insect cuticles with an oxidizing agent prior to enzymatic hydrolysis.

Preferably, in the method according to the invention, the oxidizing agent used in the treatment of the cuticles is selected from the group constituted by hydrogen peroxide, potassium permanganate, ozone and sodium hypochlorite, even more preferably hydrogen peroxide.

Advantageously, when the oxidizing agent is hydrogen peroxide, the quantity of this agent introduced for treating the insect cuticles is such that the hydrogen peroxide content is comprised between 1 and 33% by weight based on the total weight of insects, preferably between 2 and 12% by weight based on the total weight of insects, preferably of the order of 6% by weight.

Preferably, treatment of the insect cuticles with the oxidizing agent is carried out in the presence of water, such as fresh water. Advantageously, the quantity of water used in the treatment of the cuticles is determined as follows: the ratio of the volume of water in mL to the weight of insect in g is preferably comprised between 0.3 and 10, more preferably between 0.5 and 5, even more preferably between 0.7 and 3, even more preferably of the order of 1.

Treatment of the insect cuticles with the oxidizing agent can be carried out during one or more of the following steps:
- concomitantly with scalding and/or after the scalding step, more preferably concomitantly with scalding. Alternatively, concomitantly with blanching and/or after the blanching step, more preferably concomitantly with blanching. More particularly, when treatment of the insect cuticles is carried out during scalding or blanching, the oxidizing agent can advantageously be added to the water used for scalding the insects.
- before, concomitantly and/or after grinding. More particularly, when treatment of the insect cuticles is carried out during grinding, the oxidizing agent can advantageously be added to the water used for grinding.
- before and/or concomitantly with pressing.
- during a special step of treatment of the insect cuticles.

Advantageously, enzymatic hydrolysis can be followed by a step of heat inactivation for the purpose of inactivating the enzyme or the enzyme mixture used in enzymatic hydrolysis.

At the end of a method according to the invention, the chitin can be recovered by pressing or centrifugation of the enzymatic hydrolysis reaction mixture. At this stage, a chitin co-product is also recovered, namely a hydrolysate.

A preferred embodiment of a method according to the invention is described in more detail below.

In particular, this preferred embodiment describes various advantageous steps for a method according to the invention, such as steps of mild purification of the chitin: a second pressing, washing operations, optional filtration and drying.

Finally, as chitin is generally marketed in the form of powder, a second grinding can also be carried out. The latter can also be carried out to promote the deacetylation reaction, for preparing chitosan from chitin. The conditions of the deacetylation reaction are described more fully in step 10 of the preferred embodiment described in detail below.

A particularly advantageous method for the production of chitin from insect cuticles comprises the following steps:
a) killing the insects,
b) grinding the insects,
c) pressing the insects,
d) enzymatic hydrolysis of the insect cuticles with a proteolytic enzyme,
e) recovery of the chitin,
where the insect cuticles can optionally be treated with an oxidizing agent before step d).

The preferred embodiments of the various steps a) to e) as well as treatment with the oxidizing agent are as stated above or in the corresponding step in the preferred embodiment below.

The invention also relates to a chitin, such as a chitin obtainable by a method according to the invention. Owing to the mild conditions used in the method according to the invention, this chitin has a structure close to that of the chitin as it occurs in the natural state in the insect cuticle while having a high degree of purity, such as a degree of purity comprised between 40 and 90%, preferably between 50 and 90%, more preferably comprised between 60 and 85%, and even more preferably of the order of 80%.

The chitin according to the invention has at least any one of the following advantageous properties:
- an ash content less than 4%, preferably less than 3.5%, more preferably less than or equal to 2.5% (especially when the chitin is prepared from vegetarian insects), more preferably less than 2%, and even more preferably less than or equal to 1.5% (especially when chitin is prepared from *T. molitor*), and even more preferably less than 1% by weight based on the total weight of dry matter,
- degree of purity (or gravimetric purity) comprised between 40 and 90%, preferably between 50 and 90%, more preferably comprised between 60 and 85%, and even more preferably of the order of 80%,
- a functional surface abundance having a (C—O)/(C—H) ratio comprised between 0.30 and 0.56, preferably between 0.31 and 0.53,
- lipid content ≤14% by total weight based on the total weight of dry matter,
- lipid content ≤5% when chitin is prepared from non-flying insects,
- total amino acids ≤1.5%,
- total amino acids ≤16% when chitin is prepared from flying insects,
- relative abundance of at least any 3 amino acids from Ala, Gly, Leu, Pro, Ser, Tyr, Val ≤10%,
- relative abundance of Leu, Pro, Val ≤10% when chitin is prepared from *T. molitor*,
- relative abundance of Ala ≤12% when chitin is prepared from *T. molitor*,
- colorimetric purity ≥40%,
- colorimetric purity ≥50% when chitin is prepared with the enzyme Prolyve NP in enzymatic hydrolysis,
- purity by difference ≥45%, preferably ≥49%,
- purity by difference ≥52% when chitin is prepared from *T. molitor*,
- purity by difference ≥70% when chitin is prepared from flying insects,
- degree of acetylation ≥70% and degree of crystallinity ≤1.61,
- degree of acetylation ≥70% and degree of crystallinity ≥0.42.

The chitin comprises an amino acid content less than or equal to 45%, an ash content less than or equal to 3.5%, preferably less than or equal to 2.5%, and purity by difference greater than or equal to 45%, preferably greater than or equal to 49%.

Preferably, the chitin has all the above properties.

All the units and methods of measurement of the features stated above are described in the examples, and more particularly in Example 5.

A particularly advantageous method for the production of a hydrolysate from insects, comprising the following steps:
a) killing the insects,
b) grinding the insects,
c) pressing the insects,
d) enzymatic hydrolysis of the insect cuticles with a proteolytic enzyme,
e) recovery of the hydrolysate,
where the insect cuticles can optionally be treated with an oxidizing agent before step d).

The preferred embodiments of the various steps a) to e) as well as treatment with the oxidizing agent are as stated above or in the corresponding step in the preferred embodiment below.

The invention also relates to a hydrolysate, such as a hydrolysate obtainable by a method according to the invention.

The hydrolysate according to the invention has at least any one of the following advantageous properties:
- an ash content less than 4%, preferably less than 3% by weight (especially when the hydrolysate is prepared from vegetarian insects) based on the total weight of dry matter,
- excellent digestibility, in particular pepsin digestibility, greater than 95%, preferably greater than or equal to 96% and more preferably greater than or equal to 98%, and more particularly greater than or equal to 99%, the pepsin digestibility having been measured according to a method complying with Decision 72/188/EEC;
- a protein/peptides content greater than or equal to 70%, preferably greater than or equal to 71%, and more preferably greater than or equal to 75%, and more preferably greater than or equal to 80% (in particular, when the hydrolysate is prepared from non-flying insects);
- a water-soluble protein content larger than 12,400 g/mol, less than 20%, preferably less than 18% by weight based on the total weight of water-soluble proteins;
- a lipid content less than 14%, preferably less than 10%, more preferably less than or equal to 5% (especially when the hydrolysate is prepared from non-flying insects), more preferably less than or equal to 2%, and even more preferably less than or equal to 1%;
- a composition in which the most abundant amino acids are proline, alanine, leucine, aspartic acid, glutamine and/or valine. By "most abundant" is meant a relative quantity of the amino acid in the composition greater than 5%, preferably greater than 7% by weight based on the total weight of amino acids.

The high proline content proves particularly interesting;
- relative abundance of at least any 5 amino acids selected from Asp, Glu, Ala, Gly, Leu, Pro, Tyr, Val, Lys ≥6%;
- relative abundance of at least any 3 amino acids selected from Asp, Glu, Ala, Leu, Pro, Tyr, Val ≥8%.

More particularly, by "water-soluble proteins" is meant, among the proteins (or crude proteins), those that are soluble in an aqueous solution the pH of which is comprised between 6 and 8, advantageously between 7.2 and 7.6.

Preferably, the aqueous solution is a buffer solution the pH of which is comprised between 6 and 8, advantageously between 7.2 and 7.6.

Preferably, the buffer solution is a phosphate buffered NaCl solution, the pH of which is equal to 7.4±0.2.

The hydrolysate comprises at least 40% of proteins, at a maximum 10% preferably at a maximum 8% of ash, and a water-soluble protein content larger than 12,400 g/mol less than 50%, preferably less than 43%.

By "vegetarian insect" is meant an insect that does not have animal proteins in its usual diet. By way of an example of vegetarian insects, the Coleoptera, Lepidoptera or Orthoptera may be mentioned.

By "flying insect" is meant an insect that is capable of flying when adult, in contrast to an insect called "non-flying". By way of an example of flying insects, the Lepidoptera or Diptera may be mentioned. By way of an example of non-flying insects, the Coleoptera or Orthoptera may be mentioned.

All the units and methods of measurement of the features stated above are described in the examples, and more particularly in Example 5.

Preferably, the hydrolysate has all the above properties.

It will be noted in particular that the hydrolysate according to the invention can be distinguished from any other type of hydrolysate by its glucosamine content, and/or a derivative thereof (preferably N-acetylglucosamine), more particularly a content greater than or equal to 0.01%, preferably greater than or equal to 0.08% by weight based on the total weight of dry matter of the hydrolysate.

In the present application, any reference to a regulation or a directive concerns said regulation or said directive as in force on the filing date of the present application.

The hydrolysate can advantageously be supplemented with additives to balance its nutritional profile so as to make it suitable for different types of animals.

The hydrolysate can advantageously be concentrated and then dried in order to obtain a dried hydrolysate. Alternatively, the hydrolysate can be in liquid form. These hydrolysates can be used as a foodstuff or a food ingredient in particular for animals, or alternatively they can be processed, for example to isolate amino acids.

A particularly advantageous method for the production of chitosan from insect cuticles comprises the following steps:
a) killing the insects,
b) grinding the insects,
c) pressing the insects,
d) enzymatic hydrolysis of the insect cuticles with a protease,
e) recovery of the chitin,
f) deacetylation of the chitin recovered,
g) recovery of the chitosan,
where the insect cuticles can optionally be treated with an oxidizing agent before step d).

The preferred embodiments of the various steps a) to g) as well as treatment with the oxidizing agent are as stated above or in the corresponding step in the preferred embodiment below.

The invention also relates to a chitosan obtainable by a method according to the invention.

The chitin and/or chitosan obtainable by a method according to the invention can advantageously be used in various applications:
- in cosmetic, pharmaceutical, nutraceutical or dietetic compositions,
- as biomaterials for treating burns, as second skin, for making corneal dressings or suture materials,
- as filtering, texturizing, flocculating and/or adsorbent agents in particular for water filtration and purification.

According to a preferred embodiment of the invention, the method comprises the following steps, described schematically in FIG. 1. It should be noted that certain steps are indicated as optional in this preferred embodiment.

Step 1: Killing the Insects

This killing step 1 makes it possible to kill the insects while reducing the microbial load (reducing the risk of deterioration and health risk) and by inactivating the internal enzymes of the insects which can trigger autolysis, and thus a rapid browning thereof.

Killing can be carried out by scalding.

The insects, preferably larvae, are thus scalded with water for 2 to 20 min, preferably 5 to 15 min. Preferably, the water is at a temperature comprised between 95 and 105° C., preferably 100° C.

The quantity of water introduced in this scalding step 1 is determined as follows: the ratio of the volume of water in mL to the weight of insect in g is preferably comprised between 0.3 and 10, more preferably between 0.5 and 5, even more preferably between 0.7 and 3, even more preferably of the order of 1.

Alternatively, killing can be carried out by blanching. Preferably, the insects are blanched with steam (steam nozzles or bed) at a temperature comprised between 80 and 130° C., preferably between 90 and 120° C., more preferably between 95 and 105° C., even more preferably 98° C. or with water at a temperature comprised between 95 and 105° C., preferably 100° C. (by spray nozzles) or in mixed mode (water+steam) at a temperature comprised between 80 and 130° C., preferably between 90 and 120° C., more preferably between 95 and 105° C. The residence time in the blanching chamber is comprised between 1 and 15 minutes, preferably between 3 and 7 min.

In this step, it is also possible to treat the insect cuticles using scalding or blanching water comprising the oxidizing agent according to the details indicated in the intermediate step below.

Intermediate Step (Optional): Treatment of Cuticles with the Oxidizing Agent

A special step of treatment of the cuticles with the oxidizing agent can be incorporated in the method. Advantageously, this intermediate step of treatment of the cuticles is carried out between the killing step 1 and the grinding step 2.

This intermediate step is preferably carried out with an oxidizing agent selected from the group constituted by hydrogen peroxide ($H_2O_2$), potassium permanganate ($KMnO_4$), ozone ($O_3$) and sodium hypochlorite (NaClO), more preferably hydrogen peroxide.

According to a first embodiment, at the end of step 1, when the latter is carried out by scalding, the oxidizing agent is introduced directly into the scalding tank, after optional cooling of the scalding water to a temperature of the order of 40 to 60° C., preferably of the order of 50° C.

The hydrogen peroxide as marketed is usually in the form of an aqueous solution, for example a solution at 30% by weight based on the total weight of water.

The quantity of hydrogen peroxide introduced for the treatment is such that the hydrogen peroxide content is comprised between 1 and 33% by weight based on the total weight of insects, preferably 2 to 12% by weight based on the total weight of insects, preferably of the order of 6% by weight.

According to a second embodiment, the insects are removed from the scalding tank, sieved and reintroduced into a tank.

The hydrogen peroxide is then introduced into the tank in the form of a dilute aqueous solution, the hydrogen peroxide content then being comprised between 1 and 33% by weight based on the weight of water, preferably 2 to 12% by weight based on the weight of water, and preferably of the order of 6% by weight.

Step 2: Grinding

The insects are removed from the scalding or treatment tank or from the blanching chamber, then they are sieved, and placed in a grinder, such as a knife mill, making it possible to reduce the insects to particles.

In order to facilitate the grinding, a quantity of water can be added. This quantity of water is similar to that introduced during the scalding step 1: the ratio of the volume of water in mL to the weight of insect in g is preferably comprised between 0.3 and 10, more preferably between 0.5 and 5, even more preferably between 0.7 and 3, even more preferably of the order of 1. It is also possible to keep the scalding water and/or the water resulting from the intermediate step in order to carry out this step. This water is likely to contain the oxidant. In this case, treatment of the cuticles can take place during the scalding step 1 and the grinding step 2 or during the intermediate step of treatment of the cuticles and during the grinding step.

Preferably, on completion of the grinding, the size of the insect particles is less than 1 cm (largest particle size observable using a microscope), preferably less than 0.5 cm. Preferably, the size of the particle is comprised between 500 µm and 0.5 cm and even more preferably between 500 µm and 1 mm.

It is not necessary to excessively reduce the size of the particle, for example to a size less than 250 µm.

This grinding step 2 promotes access of the enzymes to their substrate.

In this step, it is possible to introduce the oxidizing agent into the grinding mill in order to treat the cuticles according to the methods indicated in the preceding intermediate step.

When treatment of the cuticles is not carried out concomitantly with grinding, during this step it is possible to add antioxidant additives that are commonly used for product preservation and stability.

Step 3: Pressing the Insect Cuticles

The wet paste originating from the grinding step 2 is then placed in a press according to a procedure which makes it possible to press and separate a juice comprising both a fat fraction and a protein fraction.

Preferably, the pressing step makes it possible to obtain a press cake comprising an oil content less than or equal to 20%, preferably less than or equal to 15%, more preferably less than or equal to 12%, even more preferably less than or equal to 10%.

Similarly, the pressing step makes it possible to obtain a press cake having a dry matter content comprised between 30% and 60%, preferably comprised between 40% and 55%, and more preferably comprised between 45% and 50%.

Any press system can be used for carrying out the pressing step, such as for example a single-screw or twin-screw press (twin-screw press of the Angel type), a filter-press (filter-press of the Choquenet type), a platen press, etc. These systems are well known to a person skilled in the art, who is able to determine the pressing conditions in order to obtain the oil and/or water contents mentioned above.

If the wet paste from the grinding step 2 was obtained with water comprising the oxidant, it can be advantageous to eliminate at least a part of this oxidant before the pressing step 3.

This pressing step 3 can optionally be carried out before the grinding step 2 starting from the scalded insects. However, it is advantageous to carry out the pressing step 3 after the grinding step 2.

This pressing step 3 therefore makes it possible to obtain a press juice and a press cake.

Step 4: Enzymatic Hydrolysis

The wet paste originating from the grinding step 2 or the press cake originating from the pressing step 3 is placed in a hydrolysis tank with water.

Optionally, and as will be described below, the protein fraction originating from the separating step 12 can be reintroduced in this enzymatic hydrolysis step 4, by mixing it with the press cake.

Optionally, and in the case when the scalding water does not contain oxidant, the scalding water can be recovered and reintroduced in the hydrolysis step. In fact, this water contains insect fractions that have been solubilized by the action of this scalding, and by using the latter in the hydrolysis it is possible to reduce the losses. Optionally, this water from scalding can be defatted, as certain waxes can have dissolved in the water.

The quantity of water introduced in this enzymatic hydrolysis step 4 is similar to that introduced in the scalding step 1: the ratio of the volume of water in mL to the weight of insect in g is preferably comprised between 0.3 and 10, more preferably between 0.5 and 5, even more preferably between 0.7 and 3, even more preferably of the order of 1.

Enzymatic hydrolysis is carried out with a protease, such as a commercial protease, for 4 to 8 h, more particularly for 4 to 5 h, at a pH from 6 to 8, more particularly from 6.5 to 7.5, at a temperature from 40 to 60° C., more particularly from 45 to 55° C.

The quantity of enzymes introduced in the hydrolysis step is less than 10% by weight based on the estimated total weight of dry matter entering hydrolysis, preferably less than 6%, more preferably of the order of 2%.

Proteolytic hydrolysis results in the production of a soluble phase containing the peptides, glucosamines and oligochitins and a solid residue formed from chitin, mainly chitin-polypeptide copolymer.

Step 5: Heat Inactivation

In order to stop the activity of the enzymes of the reaction and stabilize the soluble phase of the hydrolysis, heat inactivation is carried out by heating this juice between 80 and 105° for 10 to 25 min, preferably 15 to 20 minutes. According to one procedure, this heat inactivation step 5 is carried out according to the usual sterilization techniques of the agri-food industry. According to another procedure, enzyme inactivation is carried out by heating under IR or UV radiation, or by microwave heating.

Step 6: Pressing

The solid residue, predominantly composed of chitin, is recovered and then pressed in a press for maximum draining of this residue, in order to reinject this pressate into the soluble phase. The pressed residue thus formed consists essentially of chitin, mainly in the form of chitin-polypeptide copolymer.

Steps 7 and 8 (Optional): Washing and Drying

The solid residue is then washed, filtered, washed again and then dried by the conventional technologies known to a person skilled in the art.

Advantageously, the drying system is designed to protect the structure of the chitin-polypeptide copolymer: the hydrometry, ventilation and composition of the air are controlled. Advantageously, drying can be carried out in a ventilated stove at a temperature from 60 to 80° C., preferably of the order of 70° C.

Optionally, these steps can comprise a final delipidation step: the solid residue is treated with HCl in order to remove the last lipid residues, in particular the cuticular waxes.

The next steps 9 to 11 are for transforming the chitin to chitosan and therefore are only used when the desired product is chitosan.

Step 9 (Optional): Grinding

The dried solid residue, comprising predominantly chitin, is then ground, for example in a cutting (knife) mill.

The production of chitosan from chitin, by the deacetylation reaction, largely depends on the size of the chitin particles. Thus, very fine grinding of the dried solid residue before deacetylation makes it possible to increase the yields and the rate of the deacetylation reaction significantly, as shown in Table 1 below:

TABLE 1

Efficiency of deacetylation according to previous grinding of chitin

| | Grinding 30 s | Grinding 45 s | Grinding 60 s | Grinding 120 s |
|---|---|---|---|---|
| 50% of the particles | <174 µm | <117 µm | <95 µm | <67 µm |
| 90% of the particles | <310 µm | <244 µm | <157 µm | <159 µm |
| DA* | 99% | 90% | 85% | 80% |

*Measurement of the Degree of Acetylation DA

The conditions of the deacetylation carried out in the test reported in Table 1 are as follows: reaction time 4 h, 100° C., NaOH in aqueous solution at 30 vol %, in a ratio of estimated chitin:NaOH solution equal to 1:20.

Consequently, the solid residue is preferably ground to a particle size less than 200 µm, more preferably less than 160 µm.

Step 10: Deacetylation

The solid residue, optionally ground in step 9, is then placed in a reactor, to which concentrated sodium hydroxide solution is added, for 4 to 24 h, and preferably 6 to 18 h. Sodium hydroxide in aqueous solution at a content ranging from 30% to 40% is added at a ratio of weight in g of ground chitin/volume in mL of sodium hydroxide in aqueous solution comprised between 1:50 and 1:10, preferably of the order of 1:20. The tank is then heated, the deacetylation temperature being between 80 and 150° C., preferably between 90 and 120° C. and more preferably at 100° C.

Chitosan is thus obtained in powder form.

The chitosan can then undergo any operation known to a person skilled in the art allowing it to be functionalized, in particular by adding radicals (carboxylation, hydroxylation, etc.).

Step 11 (Optional): Drying

The chitosan powder is then dried at between 30 and 80° C., preferably between 50 and 70° C. and preferably at approximately 60° C., in order to obtain a powder having a dry matter content greater than 85%, more particularly greater than 90%.

The next steps are for recovering a fat fraction and a protein fraction from the juice obtained in the pressing step 3 and therefore are only used when such recovery is desired.

Step 12: Separation

The press juice undergoes one or more separating steps, in order to separate the fat fraction (insect oils) from the protein fraction (insect haemolymph proteins). These steps can be carried out by any oil separation technology well known to a person skilled in the art, such as centrifugation, decanting, separation by reverse osmosis, ultrafiltration, supercritical $CO_2$, etc., or a combination of several of these technologies.

Separation of the fat fraction can be complex, in view of the presence of oils of very varied compositions in insects, and the fatty acids can have short chains (C2-C5) as well as very long chains (for example, for waxes: >C25). Raising the temperature above the melting point of these oils (approximately 38° C.) during centrifugation makes it possible to solubilize this cream and facilitate separation of the fat fraction from the rest of the juice. The centrifugate then undergoes decanting according to a procedure (of the decanter or Tricanter type), for best possible separation of the oils and proteins.

These steps thus make it possible to obtain a fat fraction.

Once separated from the fat fraction, the protein fraction can be mixed with the press cake originating from the pressing step 3 just before the hydrolysis step 4. In fact, often more than 20% of the proteins are lost in the juice in the pressing step 3, hence the benefit of recovering this fraction and subjecting it to the hydrolysis step.

Step 13 (Optional): Concentration

According to one procedure, concentration is carried out by vacuum evaporation of the aqueous part. The concentrate has a dry extract greater than 10%, preferably greater than 20%. This operation facilitates drying, and additives commonly used for product preservation and stability can be added in this step.

Step 14 (Optional): Drying

The concentrate is finally dried by technologies that are known to a person skilled in the art, for example spraying/atomization ("spray-drying"), which makes it possible to obtain an extract, i.e. a dry powder of concentrate rich in peptides and glucosamines, the glucosamines in particular originating from the partial hydrolysis of chitin by $H_2O_2$ (essentially).

Figure 3:
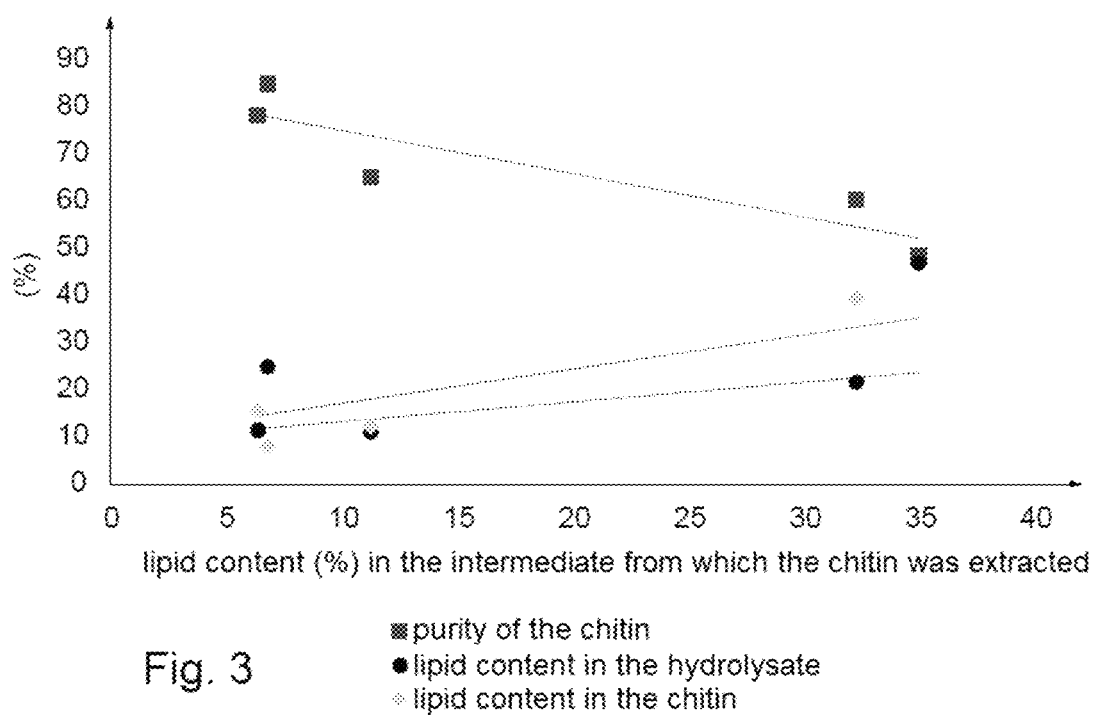
Figure 5:
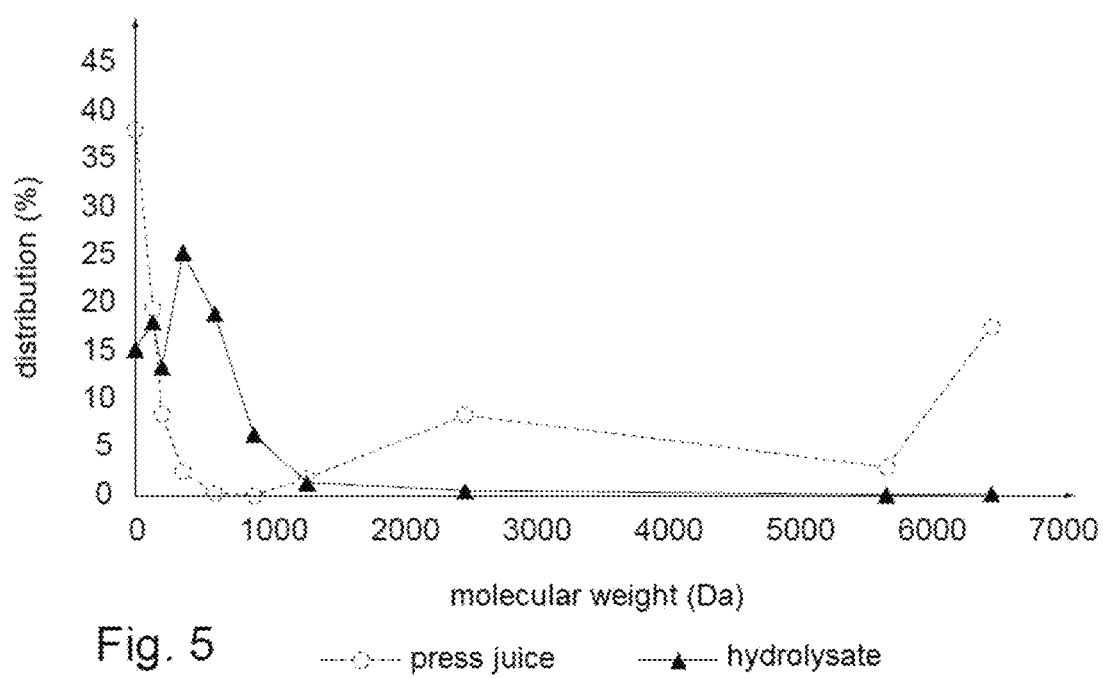
Figure 6:
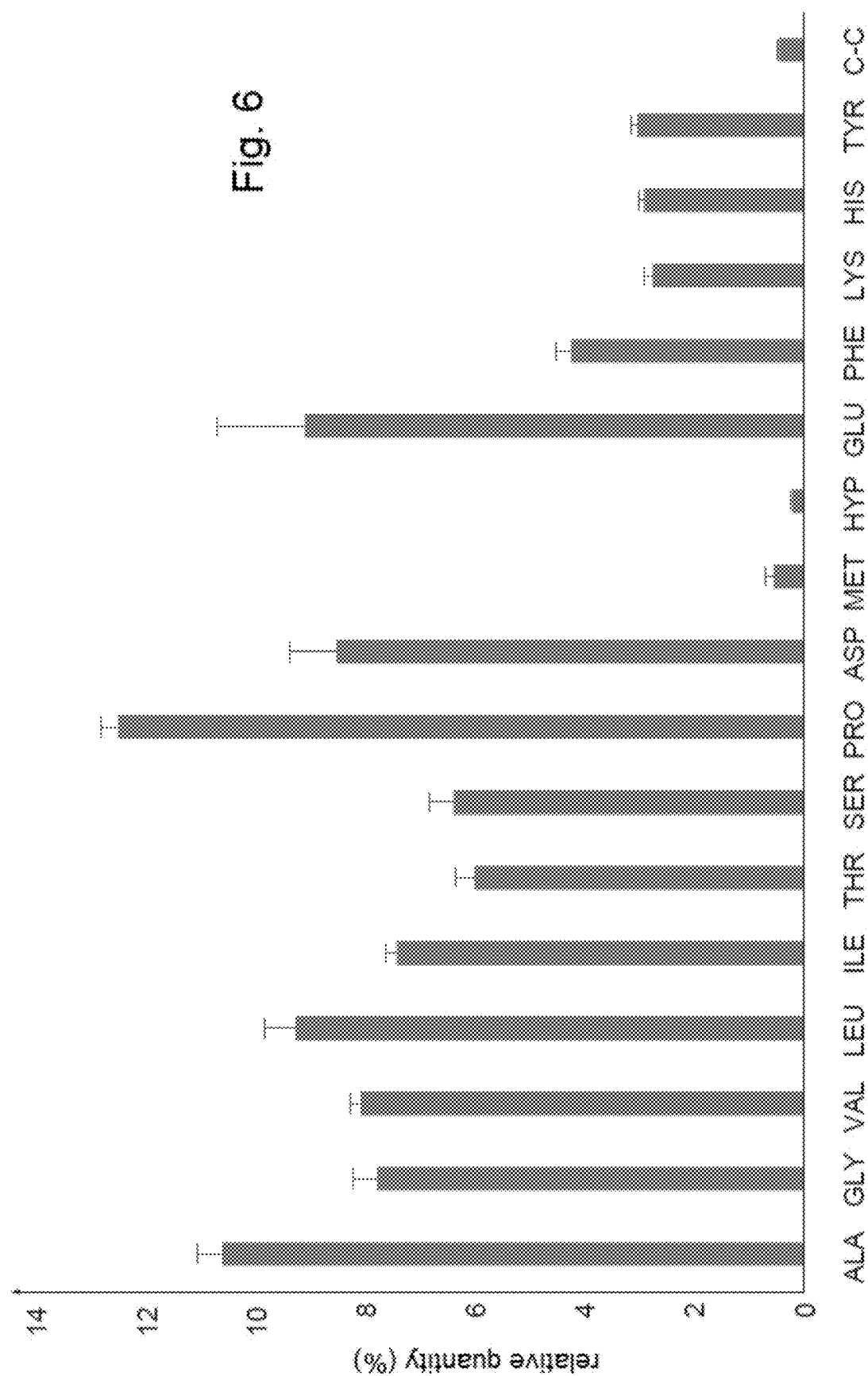
Figure 7:
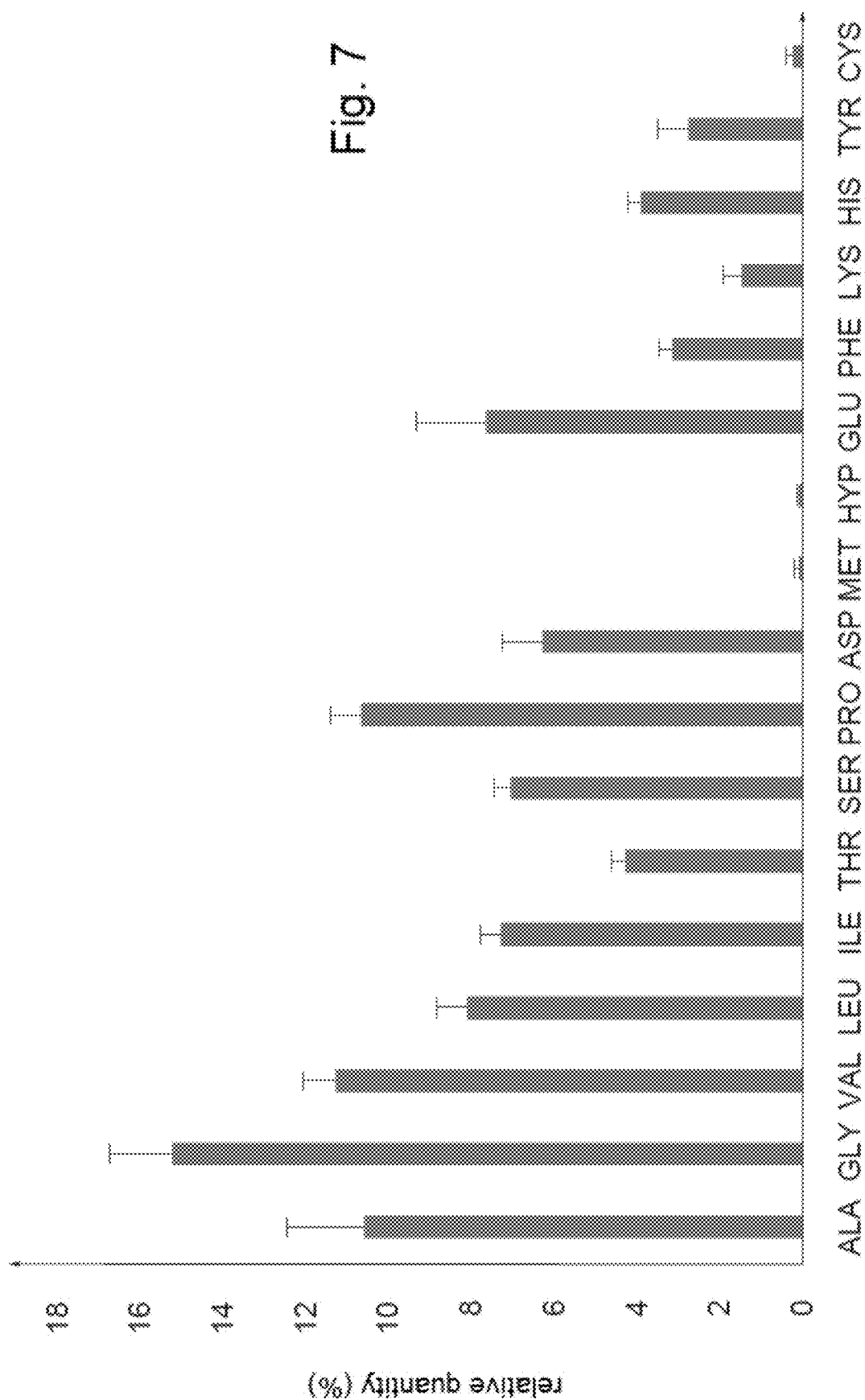
Figure 8:
Figure 18:
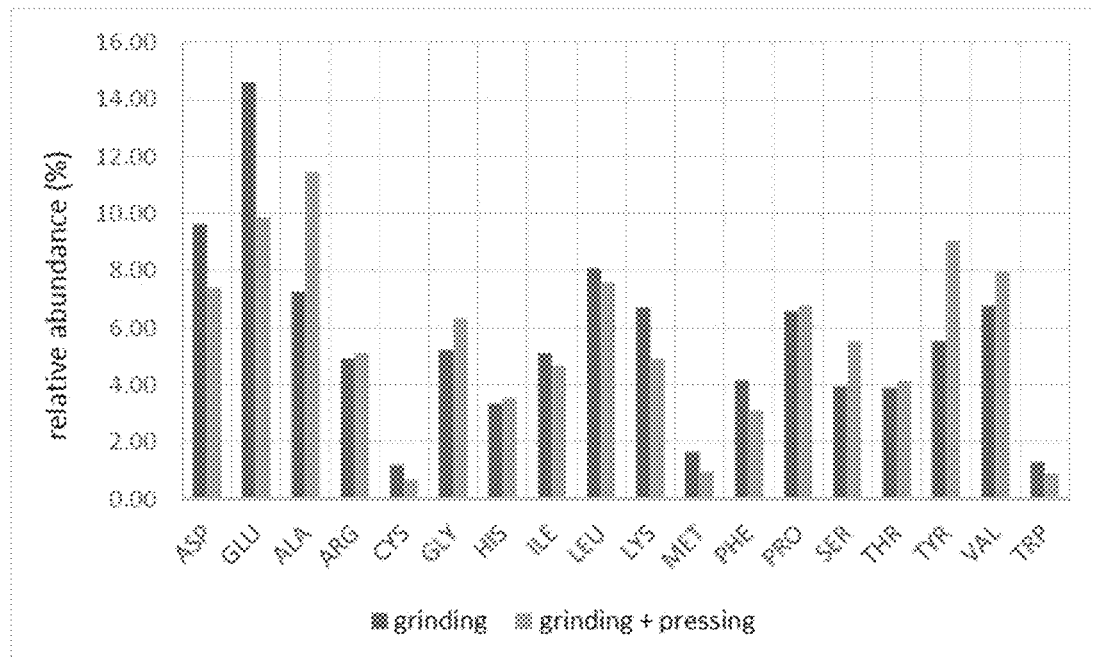
Figure 19:
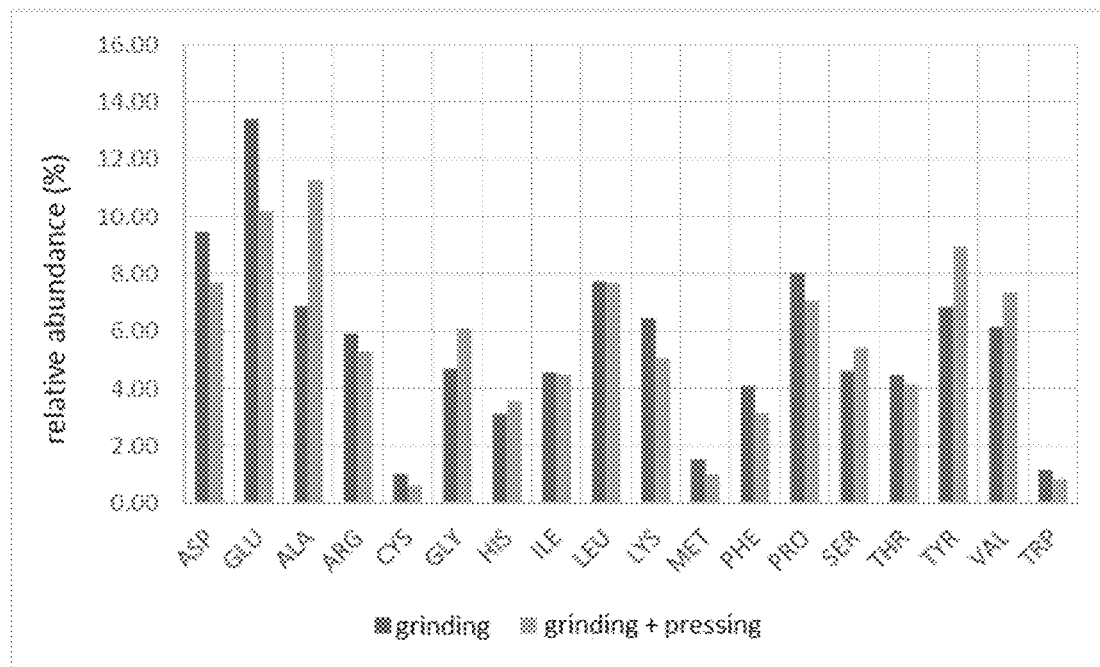
Figure 20:
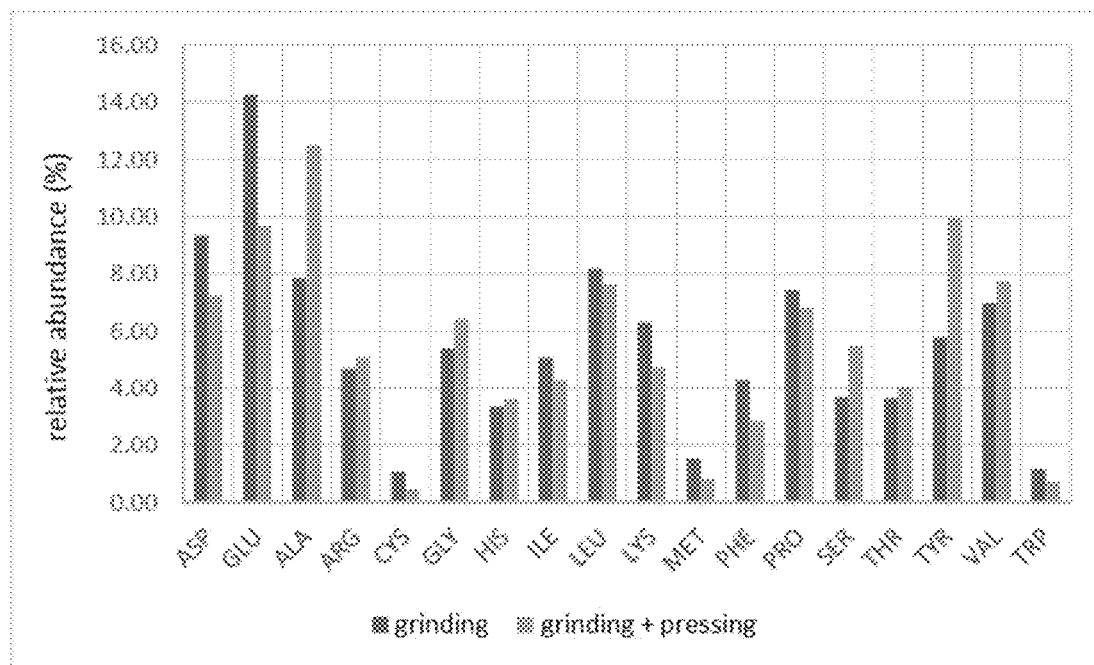
Figure 21:
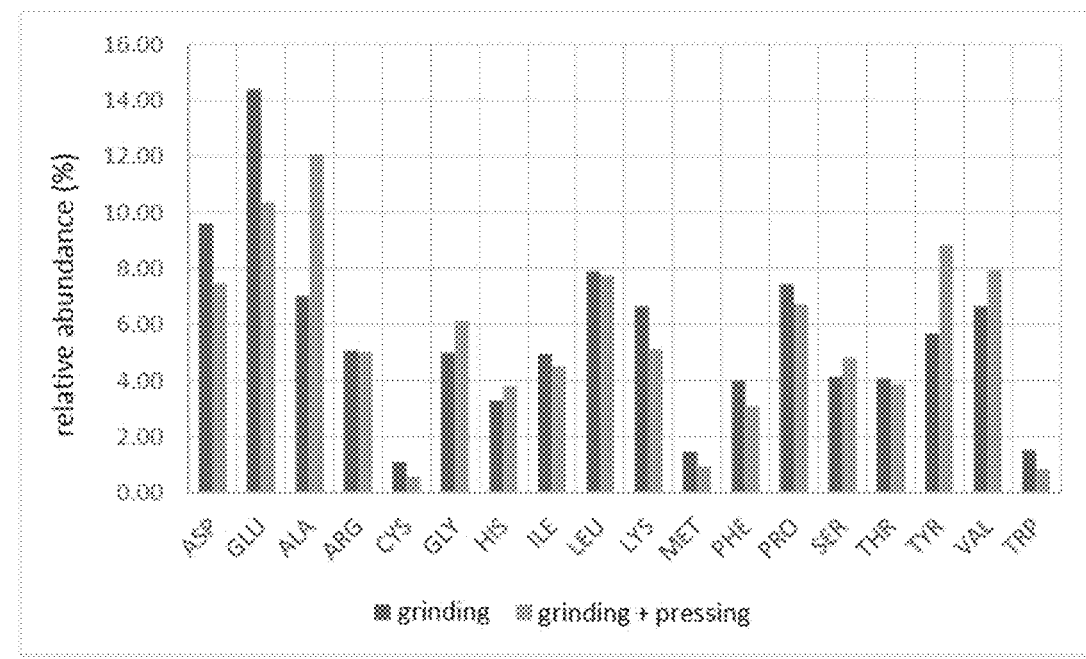
Figure 22:
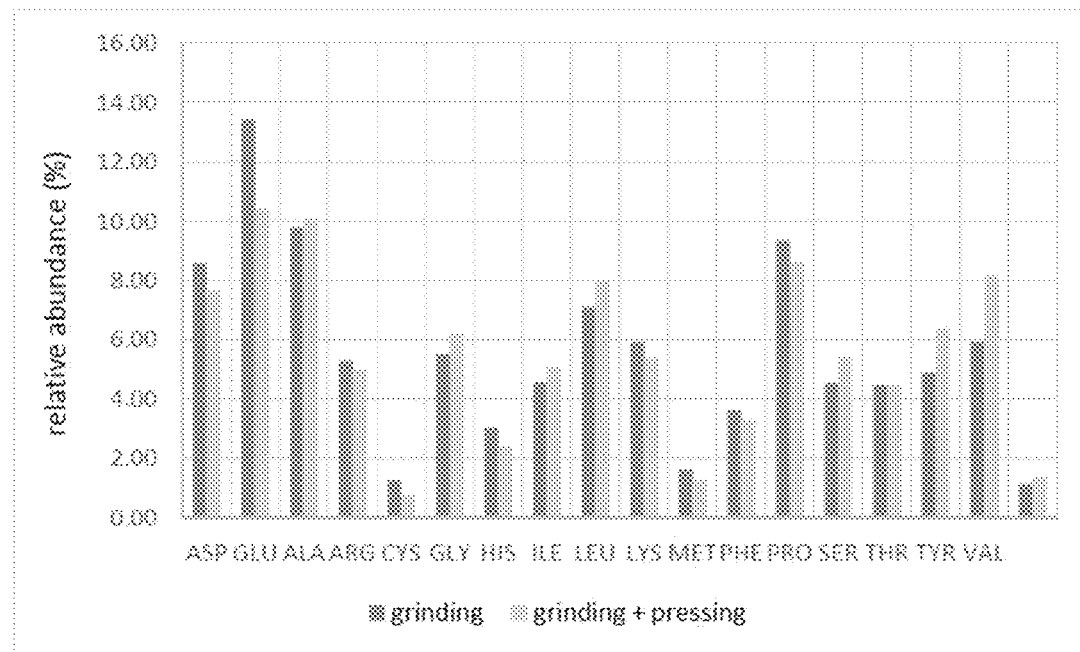
Figure 23:
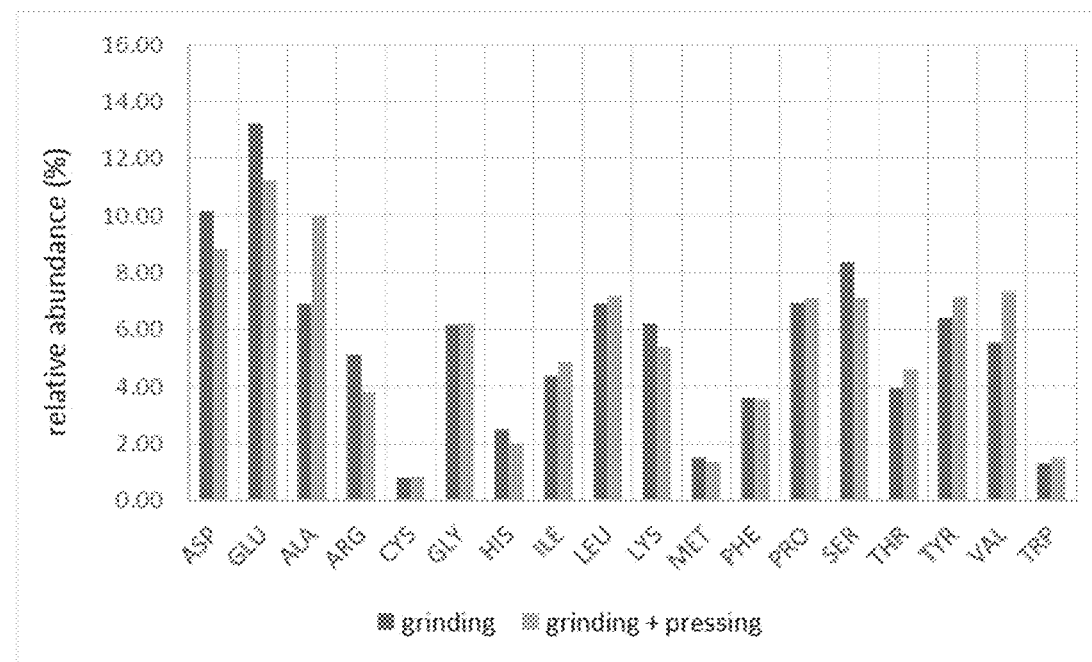
Figure 24:
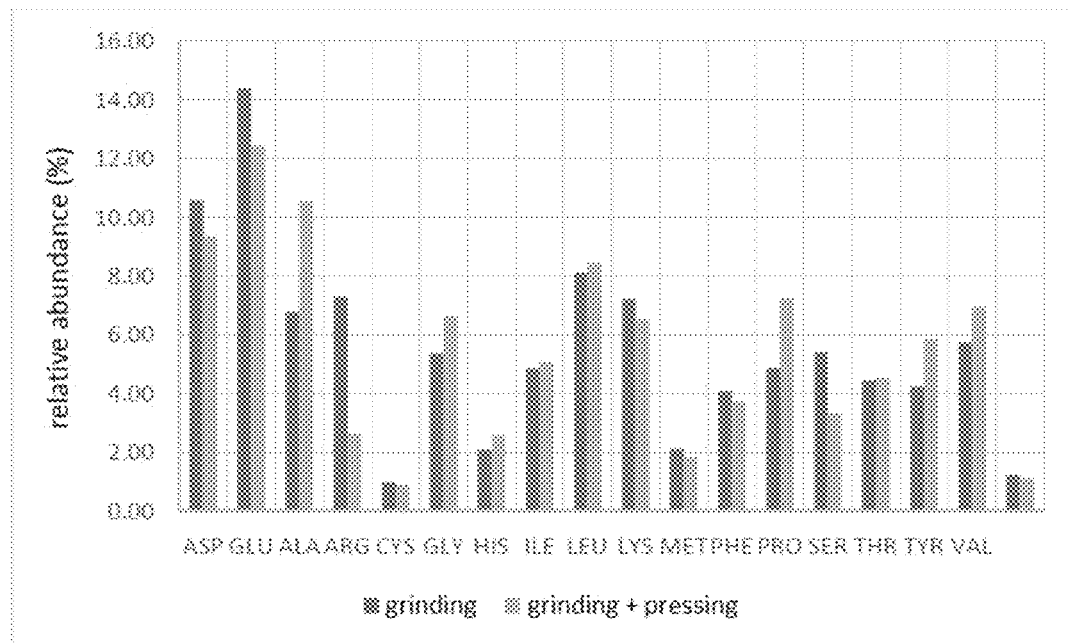
Figure 29:
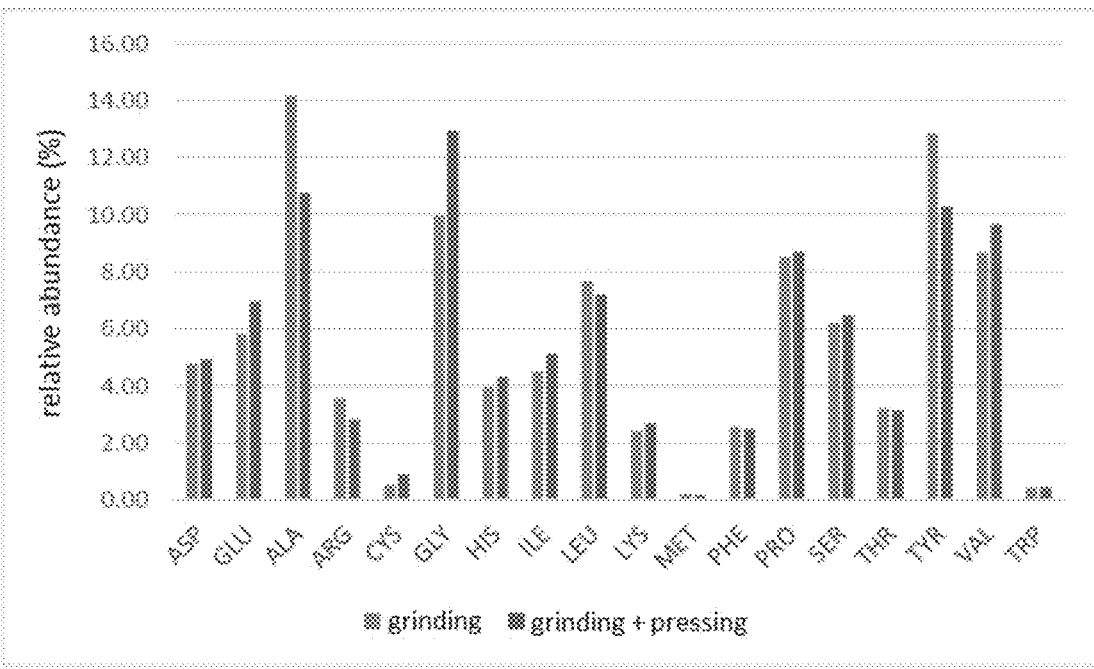
Figure 30:
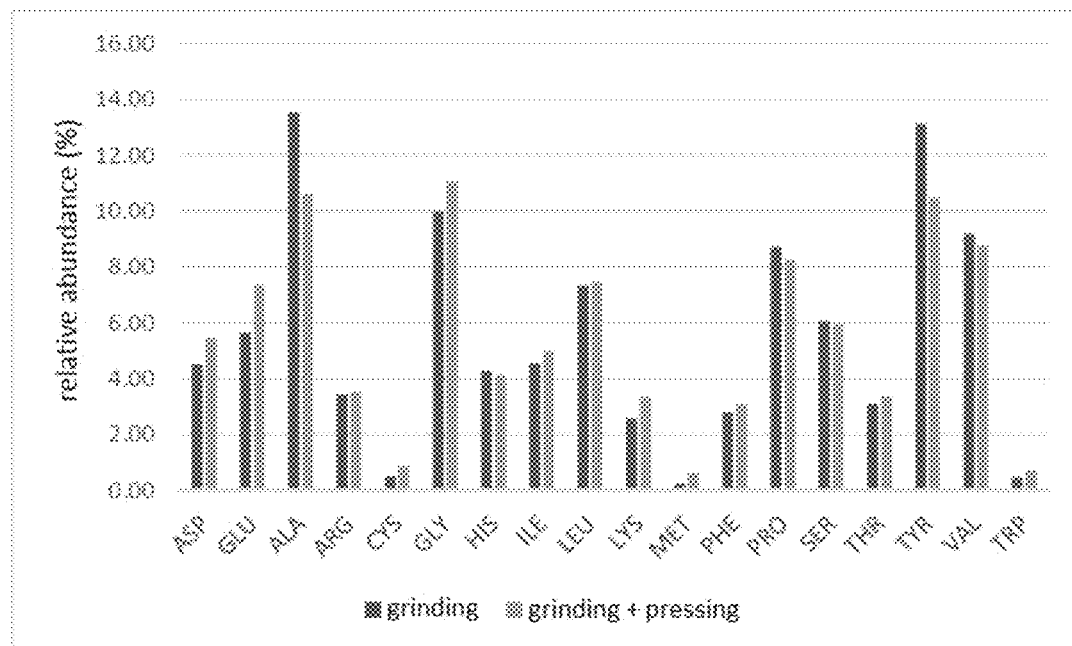
Figure 31:
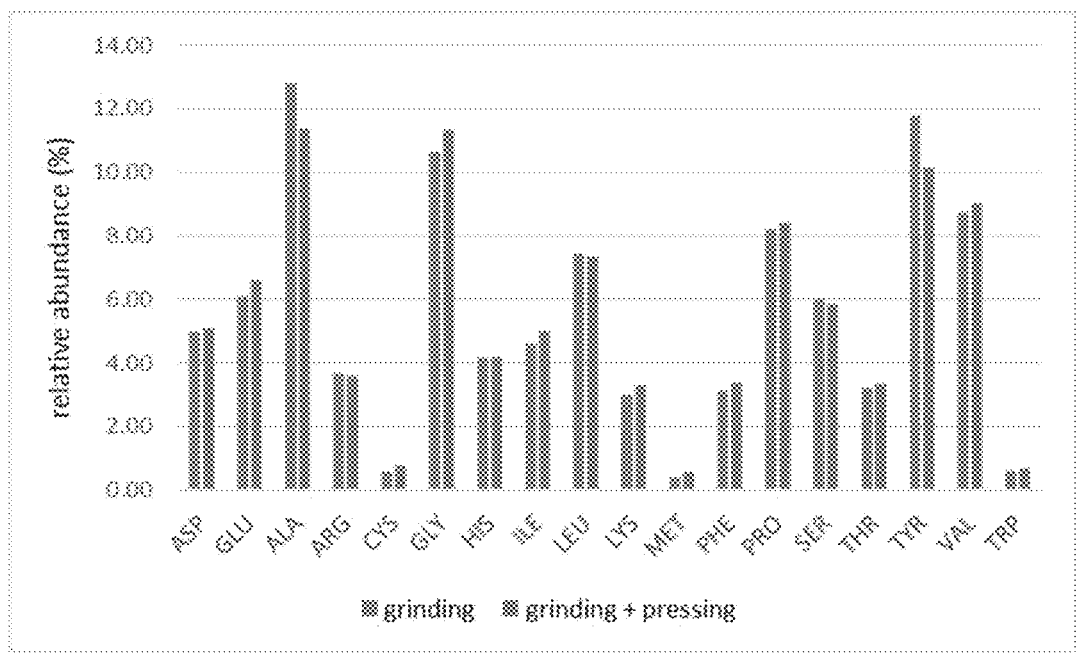
Figure 32:
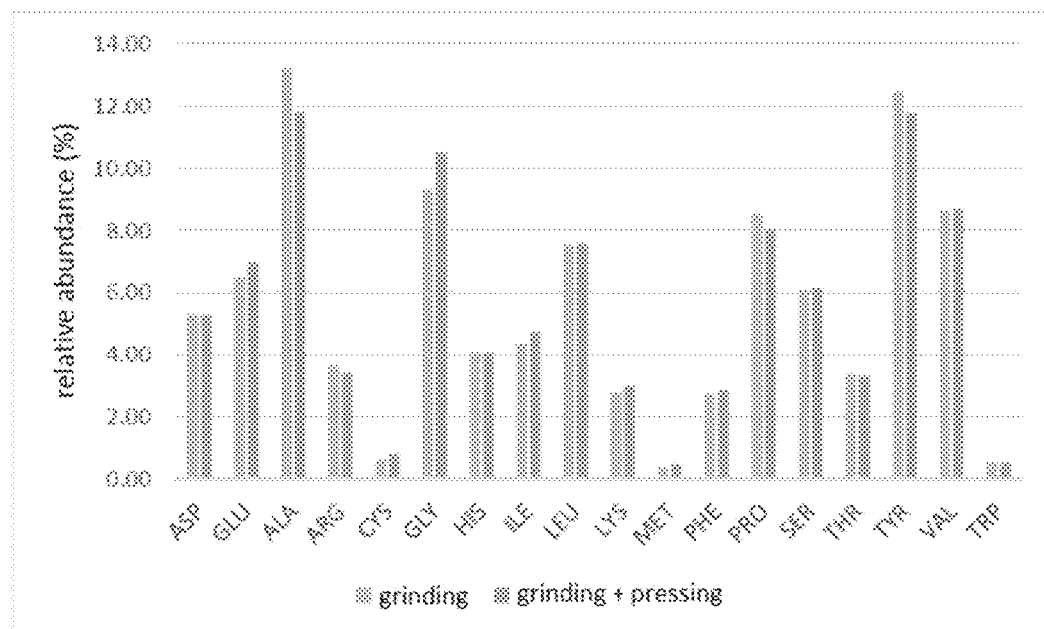
Figure 33:
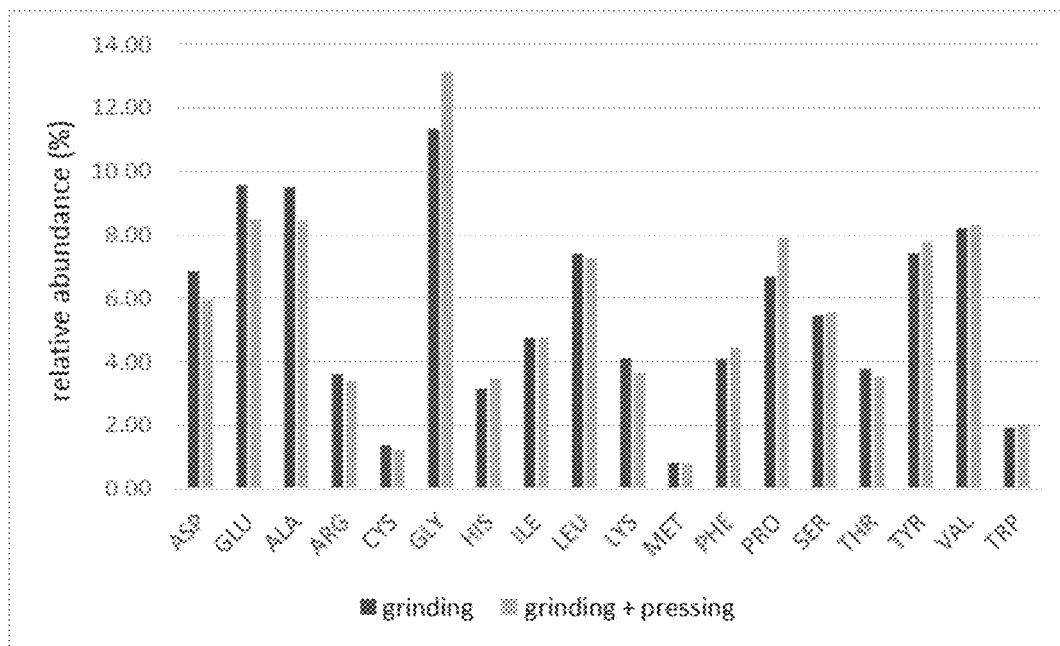
Figure 34:
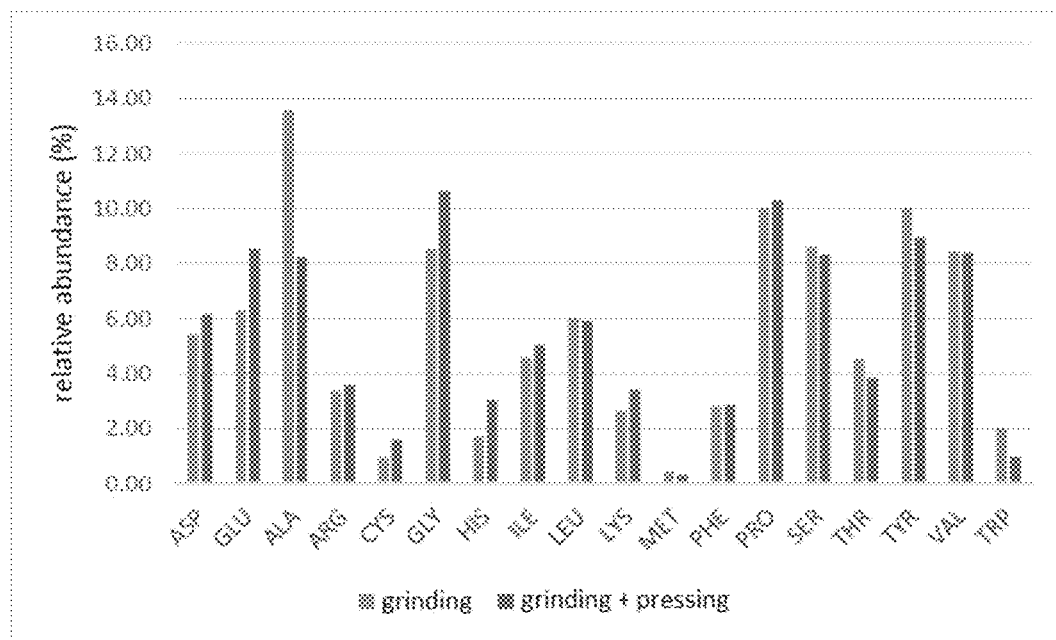
Figure 35:
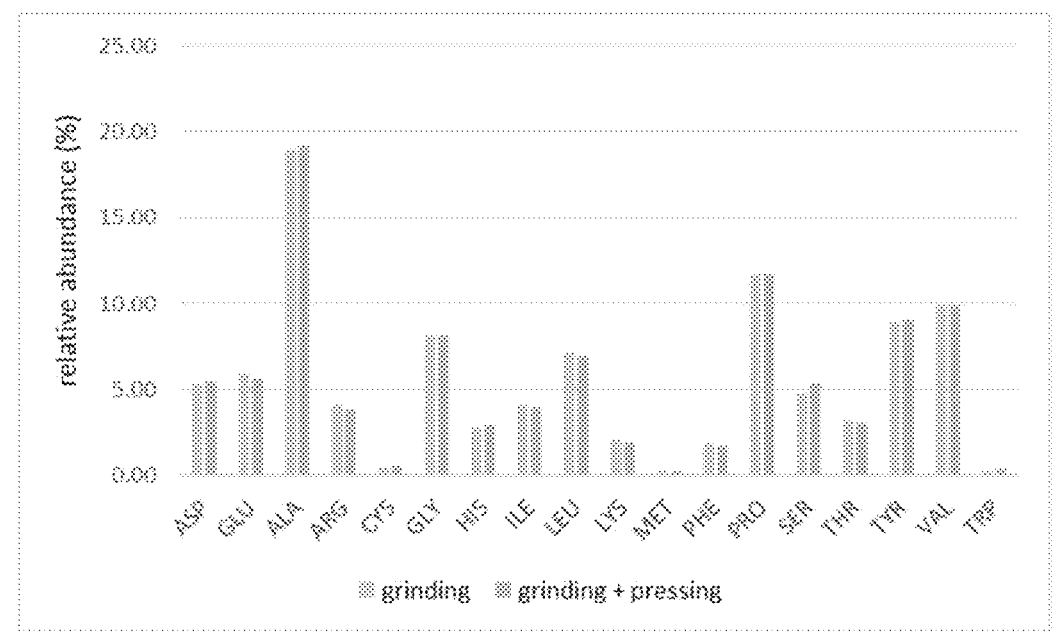
Figure 36:
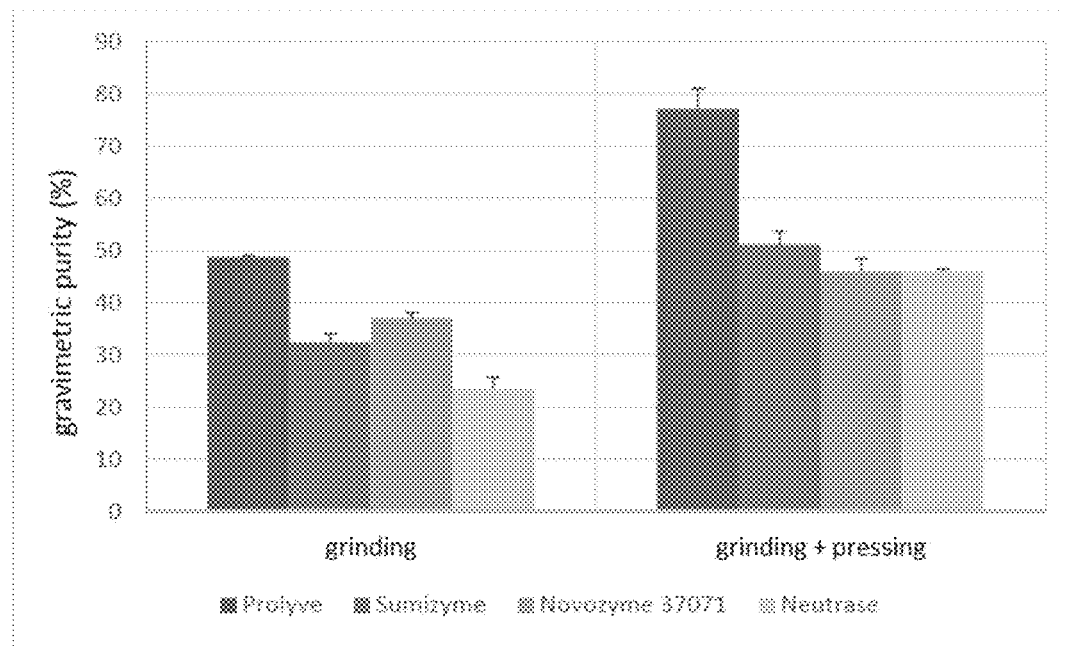
Figure 37:

Other features and advantages of the invention will become clear from the following examples, given by way of illustration, with reference to the figures, which represent respectively:

FIG. 1 is a flow chart of a preferred embodiment of the method according to the invention, FIG. 2 is a diagram comparing the degree of purity of the chitin obtained by an enzymatic method comprising one or more preliminary steps of grinding and pressing, FIG. 3 is a diagram comparing the lipid content measured in different fractions of the intermediate from which the chitin was extracted, FIG. 4 shows the distribution of the lipids in the press juice and the press cake obtained by an enzymatic method comprising preliminary steps of grinding and pressing or a preliminary step of pressing, FIG. 5 is a diagram showing the distribution of the proteins/peptides according to their molar masses (in %) in a hydrolysate according to the invention and in the press juice, FIG. 6 is a diagram showing the relative distribution of the amino acid constituting a hydrolysate according to the invention, FIG. 7 is a diagram showing the relative abundance of the amino acids in the chitin;

FIG. 8: Effect of pressing on the ash content in the hydrolysate—different insects, FIG. 9: Effect of pressing on the ash content in the hydrolysate—different enzymes, FIG. 10: Ash content in the hydrolysate with the grinding+pressing method—different insects, FIG. 11: Relative abundance of large proteins as a function of different methods and different insects for hydrolysis carried out with Prolyve, FIG. 12: Relative abundance of large proteins as a function of different methods and different enzymes applied to *T. molitor*, FIG. 13: Effect of pressing on the protein content of the hydrolysate—different enzymes, FIG. 14: Effect of pressing on the protein content of the hydrolysate—different insects, FIG. 15: Effect of pressing on the lipid content of the hydrolysate—different enzymes, FIG. 16: Effect of pressing on the lipid content of the hydrolysate—different insects, FIG. 17: Pepsin digestibility of the hydrolysates obtained—provisional, FIG. 18: TM+Prolyve: relative abundance of amino acids in the hydrolysate, FIG. 19: TM+Sumizyme: relative abundance of amino acids in the hydrolysate, FIG. 20: TM+Novozyme: relative abundance of amino acids in the hydrolysate, FIG. 21: TM+Neutrase: relative abundance of amino acids in the hydrolysate, FIG. 22: HI+Prolyve: relative abundance of amino acids in the hydrolysate, FIG. 23: GM+Prolyve: relative abundance of amino acids in the hydrolysate, FIG. 24: AD+Prolyve: relative abundance of amino acids in the hydrolysate, FIG. 25: Effect of pressing on the ash content in the chitin—different enzymes, FIG. 26: Ash content in the chitin from different insects, FIG. 27: Lipid content in the chitin, FIG. 28: Amino acid content in the chitin, FIG. 29: TM+Prolyve: relative abundance of amino acids in chitin, FIG. 30: TM+Sumizyme: relative abundance of amino acids in chitin, FIG. 31: TM+Novozyme: relative abundance of amino acids in chitin, FIG. 32: TM+Neutrase: relative abundance of amino acids in chitin, FIG. 33: HI+Prolyve: relative abundance of amino acids in the hydrolysate, FIG. 34: GM+Prolyve: relative abundance of amino acids in the hydrolysate, FIG. 35: AD+Prolyve: relative abundance of amino acids in the hydrolysate, FIG. 36: Gravimetric purity of chitin as a function of different methods and different enzymes applied to *T. molitor*, FIG. 37: Gravimetric purity of chitin as a function of different methods and different insects with Prolyve, FIG. 38: Colorimetric purity of chitin as a function of different methods and different enzymes with *T. molitor*, FIG. 39: Colorimetric purity of chitin as a function of different methods and different insects with Prolyve, FIG. 40: Purity by difference of the chitin, FIG. 41: Degree of acetylation of the chitin obtained by the method for *T. molitor*, FIG. 42: Degree of acetylation of the chitin obtained by the method with Prolyve, FIG. 43: Imaging of the cuticle by two-photon fluorescence microscopy, FIG. 44: Degree of crystallinity of the chitins obtained, and FIG. 45: Size of the proteins in the hydrolysate.

EXAMPLE 1: EXAMPLE OF A METHOD ACCORDING TO THE INVENTION 600 g of *T. molitor* larvae are introduced into a beaker, placed in a water bath at 100° C. containing 600 mL of water, brought to the boil beforehand. After 5 minutes, the beaker is removed from the water bath, the larvae are drained, and then mixed with a volume of water of 600 mL. The liquid thus obtained is pressed with a twin-screw press of the Angel type under the following conditions:

Speed=82 rev/min;

W (energy)=3 HP (horsepower) or $2.68 \times 10^6$ J;

Porosity (approx.)=0.5 mm in the first part and 0.2 mm in the last part.

A press juice and a press cake of 136.49±4.48 g wet weight are thus obtained, 100.22±0.22 g of which is used in the next steps. However, any other type of press could have been used, provided it allows the extraction and obtaining of a press cake that is substantially similar in terms of water content and/or lipid content. By way of example, other tests were carried out with the filter press of the Choquenet type having the following features:

Filtration surface area of the cell=50 cm$^2$;
Pressure=2 to 8 bar;
Temperature=20 to 80° C.,
Porosity=25 to 80 μm;
Flow rate at the end of filtration=100 to 250 mL/h.

The press cake is transferred to a Erlenmeyer flask containing 600 mL of a solution of protease (Prolyve NP conc) at 1% (relative to the wet weight of the press cake), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. Thus, 16.99±1.77 g of chitin is obtained by this method. Under these conditions, the hydrolysate (filtrate obtained after hydrolysis) represents 609.98±10.9 g with a dry matter content of 5.05%, which, after lyophilization, makes it possible to obtain 30.8±0.55 g of dry hydrolysate.

EXAMPLE 2: INFLUENCE OF THE MECHANICAL STEPS PRIOR TO ENZYMATIC HYDROLYSIS ON THE DEGREE OF PURITY OF THE CHITIN OBTAINED

Different types of mechanical pretreatment were tested, grinding ("grinding 1") alone, grinding followed by pressing, grinding followed by pressing and a second grinding ("grinding 2"), as well as pressing alone.

For pressing, a press of the Angel type described in Example 1 was used.

1. Material and Methods

Production of Chitin with One Grinding 200 g of *T. molitor* larvae are introduced into a beaker, and placed in a water bath at 100° C. containing 200 mL of water brought to the boil beforehand. After 5 minutes, the beaker is removed from the water bath, the larvae are drained, and then mixed with a volume of water of 200 mL. The liquid thus obtained is transferred to a Erlenmeyer flask containing 2 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. Thus, 8.13±0.27 g of chitin is obtained by this method.

Production of Chitin with Grinding Followed by Pressing 200 g of *T. molitor* larvae are introduced into a beaker, and placed in a water bath at 100° C. containing 200 mL of water brought to the boil beforehand. After 5 minutes, the beaker is removed from the water bath, the larvae are drained, and then mixed with a volume of water of 200 mL. The liquid thus obtained is passed into a press of the twin-screw type. 30 g of the press cake thus obtained is transferred to a Erlenmeyer flask containing 150 mL of water and 0.3 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. Thus, 4.71±0.11 g of chitin is obtained by this method.

Production of Chitin with a First Grinding ("Grinding 1") Followed by Pressing and a Second Grinding ("Grinding 2")

200 g of *T. molitor* larvae are introduced into a beaker, and placed in a water bath at 100° C. containing 200 mL of water brought to the boil beforehand. After 5 minutes, the beaker is removed from the water bath, the larvae are drained, and then mixed with a volume of water of 200 mL. The liquid thus obtained is passed into a press of the twin-screw type. The press cake thus obtained is dried for 24 hours in an oven at 70° C., and then ground to 250 μm. 10 g of the powder thus obtained is transferred to a Erlenmeyer flask containing 50 mL of water and 0.1 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. Thus, 4.93±0.12 g of chitin is obtained by this method.

Production of Chitin with Pressing Only 200 g of *T. molitor* larvae are introduced into a beaker, and placed in a water bath at 100° C. containing 200 mL of water brought to the boil beforehand. After 5 minutes, the beaker is removed from the water bath, the larvae are drained, and then passed into a press of the twin-screw type. 90 g of press cake thus obtained is transferred to a Erlenmeyer flask containing 450 mL of water and 0.9 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. Thus, 6.48±0.28 g of chitin is obtained by this method.

Production of Chitin by the Chemical Route 50 g of *T. molitor* larvae are introduced into a beaker, and placed in a water bath at 100° C. containing 50 mL of water, brought to the boil beforehand. After 5 minutes, the beaker is removed from the water bath, the larvae are drained, and then mixed with a volume of water of 60 mL. The liquid thus obtained is transferred to a 1-L vessel and 500 mL of 1M HCl solution is added. The whole is placed under stirring at 90° C. for 1 hour. The contents are then filtered and the solid residue is transferred to a 1-L bottle containing 500 mL of 1M NaOH solution; the whole is placed under stirring at 90° C. for 24 hours. The residue is then filtered and placed in a ventilated stove at 70° C. for 24 hours. Thus, 0.944±0.005 g of chemically purified chitin is obtained.

Calculation of the Degree of Purity

The degree of purity of the chitin is determined by comparing the weight of dry residue obtained relative to that resulting from chemical extraction, approximately 5% of the initial dry matter.

Measurement of the Lipid Content 2 g of sample is placed in a beaker, to which 0.2 g of $Na_2SO_4$ and 15 mL of $CHCl_3$/MeOH (2/1 v/v) are added. The whole is placed under magnetic stirring for 20 minutes, then the solution is filtered, and the residue is again placed in the beaker with 10 mL of $CHCl_3$/MeOH (2/1 v/v). The whole is placed under magnetic stirring for 15 minutes, then the solution is filtered, the solvent phases are combined and evaporated to constant weight. The lipid content is determined as a percentage by weight after extraction-evaporation relative to the initial weight of the sample (2 g).

2. Results

As can be seen from FIG. 2, the method has an influence on the purity of the chitin obtained, the best results being obtained with minimal pressing. The best result is obtained with grinding followed by pressing, namely a chitin having a degree of purity of 78% and the poorest with grinding alone, namely a chitin having a degree of purity of 48%.

Finer analysis of the intermediate from which the chitin was extracted shows that a low lipid content promotes greater purity of the chitin obtained (FIG. 3). By "intermediate" is meant the product entering enzymatic hydrolysis, i.e. originating from the last step before hydrolysis, namely according to the aforementioned methods of production, grinding step 1 or 2 or the pressing step.

Analysis of the lipid content in the chitin and the hydrolysis juice in fact shows that as a function of the initial lipid content present in the intermediate, the lipid content in the chitin is relatively stable, from 7 to 15%, whereas the lipid content in the hydrolysate varies from 11 to 47% (FIG. 3).

More particularly, if the intermediate has a lipid content of 35%, then:
 the chitin that will result from hydrolysis will only be 50% pure and will comprise 10% lipids, and
 the lipid content of the hydrolysate will itself be close to 40%.

However, if the lipid content of the intermediate is 7%, then:
 the chitin obtained after hydrolysis will have a purity of 80% and will have a lipid content of 8% and the hydrolysate will also have a low lipid content, of the order of 10%.

This indicates that when the initial lipid content is high, greater than 12%, the enzyme responsible for hydrolysis is caused to hydrolyse not only the proteins, but also the lipids by catalytic promiscuity. Thus, a similar lipid content in the chitin is obtained, namely 8.6 and 7.9%, in cases when the initial lipids were 35 and 7% respectively. However, the purity of the chitin passes in this case from 48 to 84% respectively. Thus, of the 52% of impurities on the one hand and 16% on the other hand, 8% on average are due to the lipids, and the quantity of proteins still attached to the chitin is therefore 38 points higher in the case when more lipids were present in the intermediate subjected to hydrolysis.

Finally, the importance of grinding upstream of pressing can also be studied (FIG. 4). Thus, it can clearly be seen that the distribution of the lipids between the cake and the press juice is far more effective, 12.9 versus 87.1, against 42.7 versus 57.3 when a preliminary grinding was carried out.

EXAMPLE 3: ANALYSIS OF THE HYDROLYSATE

A detailed analysis was carried out on the hydrolysate obtained in Example 1.

1. Glucosamine Content

The content of glucosamines and certain other sugars in the hydrolysate was analysed by gas chromatography after methanolysis and silylation.

Procedure:

10 mg of the sample and 50 µg of internal standard are placed in 500 µL of a methanol/3N hydrochloric acid mixture for 4 hours at 110° C. (or 24 hours at 130° C.). The mixture is then neutralized with $Ag_2CO_3$. 50 µL of acetic anhydride is added in order to re-acetylate any osamines present. After holding overnight in darkness at ambient temperature, the samples are centrifuged (15 min, 3000 rpm) and the supernatant is evaporated. The compounds are then dissolved in 100 µL of pyridine and incubated overnight at ambient temperature with 100 µL of BSTFA (Supelco). The reagents are then evaporated and the residue is taken up in 700 µL of $CH_2Cl_2$ and injected in GC.

Temperature programme: 1 minute at 120° C., gradient of 1.5° C./minute up to 180° C., then 2° C./minute up to 200° C.

Detection: FID

Column: HP-5MS (30 m, 0.25 mm inside diameter)

Internal standard: myo-inositol

The various contents were measured and calculated in two different ways (Table 2). It can be seen that glucosamine is contained in the hydrolysate at a content of 0.1-0.15% by weight and with a ratio of 0.04-0.05 relative to glucose.

TABLE 2

| | Distribution of glucosamine, mannose and glucose in the hydrolysate | | | |
|---|---|---|---|---|
| | Methanolysis at 110° C. | | Methanolysis at 130° C. | |
| | % by weight | Molar ratio | % by weight | Molar ratio |
| Glucose | 1.6 ± 0.3 | 1 | 2 ± 0.4 | 1 |
| Mannose | 0.3 ± 0.05 | 0.15 ± 0.005 | 0.4 ± 0.08 | 0.15 ± 0.007 |
| Glucosamine | 0.1 ± 0.02 | 0.04 ± 0.007 | 0.15 ± 0.04 | 0.05 ± 0.003 |

2. Size of the Proteins

The size of the proteins/peptides in the hydrolysate was evaluated by HPLC, Shimadzu 20A apparatus, at ambient temperature, on a Superdex Peptide 10/300 GL column, in buffer of acetonitrile (ACN) 30%, trifluoroacetic acid (TFA) 0.1%, with a flow rate of 0.4 mL/min. Detection was carried out at 205 nm and the sample volume injected was 20 µL.

Moreover, the size of the proteins/peptides in the press juice prepared in Example 1 was also evaluated under identical conditions for purposes of comparison.

Comparison of the size of the proteins between the press juice and the hydrolysate (FIG. 5) clearly shows that the bulk, 76%, of the peptides present in the hydrolysate have a molar mass comprised between 130 and 900 Da. However, the proportion of proteins of low digestibility (of molar mass greater than 1300 Da) is reduced from 31% to 2%. Likewise, the proportion of peptides having a bitter character (of molar mass less than 130 Da) drops from 38% to 15%. The criteria of digestibility and palatability are therefore improved by the proposed enzymatic treatment.

3. Digestibility

The level of pepsin digestibility of the hydrolysate is estimated at 99.6% of the total proteins. It was measured by an external laboratory, the method used complies with Directive 72/199/EEC and was carried out without defatting.

4. Protein Content

The protein content in the hydrolysate is estimated at 84.8%. It was measured by an external laboratory, by the Kjeldahl method with a correction factor of 6.25. The method used complies with EC Regulation 152/2009.

5. Lipid Content

The lipid content in the hydrolysate is estimated at 0.7±0.5%. It was measured by an external laboratory by the so-called "hydrolysis" method adapted from EC Regulation 152/2009 (method B).

6. Amino Acid Composition

The hydrolysate obtained after treatment with the various enzymes was analysed for its amino acid composition (FIG. 6). This shows a preponderance of proline, together with the presence of hydroxyproline (HYP)—metabolite of proline and amino acid absent in certain organisms, for example the crustaceans. Now, proline and its metabolite, hydroxyproline, play an essential role in metabolism, in particular by allowing the synthesis of other amino acids such as arginine and glutamate. Although most mammals are capable of synthesizing proline, production of this amino acid by neonates, birds and fishes is insufficient, which is why supplementation with proline and hydroxyproline is sometimes used for increasing the growth of certain animals. Moreover, proline is the first amino acid contained in mammalian milk, where it is present at a content of 12%, but its content in plant proteins is far less, only 2.9% in soya and 0.8% in maize. Therefore this hydrolysate is found to have a proline content as high as in milk, and well above that found in vegetable proteins.

The other amino acids present in large quantities are alanine, leucine and glutamate (with glutamine). Their relative quantities are greater than 9%. However, the sulphur-containing amino acids such as cysteine and methionine are present in low quantities, of the order of 0.5%.

The method used for determining these results (acid hydrolysis) did not make it possible to detect amino acids such as tryptophan and arginine. Moreover, asparagine was completely transformed to aspartic acid and glutamine to glutamic acid, and what is observed under the Asp and Glu peaks is in fact respectively the sum of aspartic acid and asparagine on the one hand and glutamic acid and glutamine on the other hand, initially present in the hydrolysate.

EXAMPLE 4: ANALYSIS OF THE CHITIN

A detailed amino acid analysis was carried out on the chitin obtained in Example 1.

The total content of amino acids is 32.3 g per 100 g of copolymer (determined as the sum of the amino acids). The amino acids present are predominantly valine, glycine, alanine and tyrosine (FIG. 7).

The analyses were subcontracted and the results were obtained by the method NF EN ISO 13904 for tryptophan and NF EN ISO 13903 for the other amino acids.

EXAMPLE 5: CHARACTERIZATION OF THE HYDROLYSATE AND THE CHITIN ACCORDING TO THE METHOD OF PRODUCTION USED

I. Material and Methods
a) Material
Insects
Various insects were studied:
a coleopteron: *Tenebrio molitor* (*T. molitor* or TM),
a lepidopteron: *Galleria mellonella* (*G. melonella* or GM),
a dipteron: *Hermetia illucens* (*H. illucens* or HI), and
an orthopteron: *Acheta domesticus* (*A. domesticus* or AD).
Enzymes
Various enzymes were used in the hydrolysis step.
This measurement of the enzymatic activity is based on the principle of measurement of tyrosine release at 275 nm during hydrolysis of casein by a proteolytic enzyme (Valley Research SAPU Assay method, by Karen PRATT).

$$\frac{SAPU}{g} = \frac{(\Delta A - i) \times 11}{m \times 30 \times C \times 1}$$

SAPU/g=one spectrophotometric unit of protease
$\Delta A$=correlated absorbance
i=y-axis at origin
11=final reaction volume
M=slope of the calibration curve
30=reaction time (in minutes)
C=concentration of the enzyme (g/mL) in the enzyme solution added
1=1 mL volume of the enzyme solution added The calibration curve is obtained by measuring the absorbance of tyrosine solutions of different concentrations in a phosphate buffer (0.2M, pH 7).

5 mL of a solution of casein (0.7% w/v, phosphate buffer 0.2M, pH 7, heated for 30 minutes at 90° C. and with 3.75 g/L$_{solution}$ added) is incubated with 1 mL of the enzyme solution (0.15 g in 100 mL of glycine buffer, 0.05M) to be tested at 37° C. for 30 minutes. Then 5 mL of TCA solution is added (18 g TCA, 11.35 g of anhydrous sodium acetate, 21 mL of glacial acetic acid, made up with demineralized water to 1 litre of solution), mix on a vortex, filter and measure the absorbance at 275 nm.

The control is prepared identically but without adding enzyme, 1 mL of demineralized water is added instead in order to have the same reaction volume.

The activities thus measured for the various enzymes used (Prolyve NP, Novozyme 37071, Neutrase and Sumizyme) are listed in Table 3.

TABLE 3

| Correspondence of the activities and enzyme masses of the enzymes used | | | | |
| --- | --- | --- | --- | --- |
| enzyme | Prolyve | Novozyme | Neutrase | Sumizyme |
| Desired enzymatic activity | 3789.52 | 3789.52 | 3789.52 | 3789.52 |
| Enzymatic activity/g | 3789.52 | 1662.35 | 2213.24 | 3237.19 |
| m (g) | 1.00 | 2.28 | 1.71 | 1.17 | b) Methods of Production
Method of Production with Grinding Only (Denoted "Grinding" in the Figures)
600 g of fresh insects (either larvae in the case of *T. molitor, G. melonella* or *H. illucens*; crickets in the case of *A. domesticus*) are introduced into a chamber, where they are killed with steam (115° C., 5 minutes). The insects are then introduced into a mixer and 75 mL of water is added per 100 g of insects, and the whole is then mixed. 100 g (wet weight) of product thus obtained is then introduced into a three-necked flask equipped with a condenser and a mechanical stirrer, and a proteolytic enzyme with an activity equivalent to 3789 SAPU is then added. The reaction is then heated to 45° C. for 4 hours. The temperature is then raised to 90° C. for 15 minutes, and the reaction mixture is finally filtered (0.40-0.45 µm). The residue is dried for 24 hours at 70° C.: this is therefore chitin obtained by the enzymatic route of purification; the filtrate is frozen and lyophilized: this is therefore the hydrolysate.

The method is identical whatever insect or enzyme is studied.

Method of Production with Grinding Followed by Pressing (Designated "Grinding+Pressing" in the Figures)
600 g of fresh insects (either larvae in the case of *T. molitor, G. melonella* or *H. illucens*, or crickets in the case of *A. domesticus*) are introduced into a chamber, where they are killed with steam (115° C., 5 minutes). The insects are then introduced into a mixer and 75 mL of water is added per 100 g of insects, and the whole is then mixed and pressed (twin-screw press, or filter press, or other pressing system). 100 g (wet weight) of product thus obtained is then introduced into a three-necked flask equipped with a condenser and a magnetic stirrer, 500 mL of water is added, as well as a proteolytic enzyme with an activity equivalent to 3789 SAPU. The reaction is then heated at 45° C. for 4 hours. The temperature is then raised to 90° C. for 15 minutes, and the reaction mixture is finally filtered (0.40-0.45 µm). The residue is dried for 24 hours at 70° C.: this is therefore chitin obtained by purification by the enzymatic route; the filtrate is frozen and lyophilized: this is therefore the hydrolysate.

The method is identical whatever insect or enzyme is studied.

c) Analyses

Measurement of the Ash Content

The ash content was determined by the method based on EC Regulation 152/2009 dated Jan. 27, 2009.

Measurement of the Size of the Proteins 100 mg of sample was introduced into 10 mL of phosphate/NaCl buffer (pH 7.4, 0.137 mM). The sample was stirred for one minute (vortex), centrifuged at 900 g for 1 min and then filtered through a 0.45 µm membrane. The analysis was carried out on a steric exclusion chromatography system, with the Nucleogel GFC-300 column, the eluent used is phosphate/NaCl buffer (pH 7.4, 0.137 mM), the flow rate is 1.0 mL/min, with detection by a UV detector at 280 nm.

Measurement of the Protein Content

The protein content is obtained by the Dumas method, with a conversion factor of 6.25, adapted from standard NF EN ISO 16634-1.

Measurement of the Lipid Content

The lipid content is obtained by a method adapted from EC Regulation 152/2009—method B—SN.

Pepsin Digestibility

Pepsin digestibility is measured by the method described in Directive 72/199/EC.

Relative Abundance of Amino Acids

The abundance of the amino acids was determined by a method derived from EC Regulation 152/2009 dated Jan. 27, 2009—SN. The tryptophan content was determined separately by a method adapted from EC Regulation 152/2009 dated Jan. 27, 2009—SN. The relative abundance was calculated by relating the content of each amino acid to the amino acid content.

Amino Acid Content

The amino acid content was determined by adding together the individual values obtained for each amino acid, including tryptophan.

Gravimetric Purity

Gravimetric purity is determined by comparing the weight of dry residue obtained relative to that resulting from chemical extraction, the latter being evaluated at approximately 5% of the initial dry matter.

Colorimetric Purity

The colour of the sample was estimated by analysing photographs of samples using the ImageJ software according to the three colours red, green and blue (RGB), their average representing an assessment of the true colour. A sample of prawn chitin marketed by Chitine France was taken as the standard (100% purity) and the colorimetric purity of the samples produced was calculated as a percentage of this colour (ratio of the colour of the sample to the colour of the standard).

Purity by Difference

For this measurement, the quantities of known impurities (amino acids, lipids and ash) were subtracted from the value of absolute purity (100%) to obtain the value of the purity estimated by difference; i.e. a sample that contains 30% proteins, 10% lipids and 1% ash is therefore assigned a purity of 100−30−10−1=59%.

Degree of Crystallinity

The measurements were carried out according to the WAXS (wide angle X-ray scattering) technique on Bruker D8 Advance apparatus (A25 DaVinci design) equipped with a Lynxeye XE detector. The results were interpreted following the method described in Loelovich, M. Res. Rev.: J. Chem. 2014, 3, 7-14.

Degree of Acetylation

The measurements were carried out using $^{13}C$ NMR CP/MAS (Bruker) apparatus, equipped with an 800 MHz magnet.

The results were analysed as described in Simionatto Guinesi, L.; Gomes Cavalheiro, E. T. *Thermochimica Acta* 2006, 444, 128-133 and Heux, L.; Brugnerotto, J.; Desbrières, J.; Versali, M.-F.; Rinaudo, M. *Biomacromolecules* 2000, 1, 746-751.

Measurement of Atomic and Functional Surface Abundance

The measurements were carried out using XPS Escolab 250 (VG Scientific) apparatus, equipped with an RX Ka A1 source (1486.6 eV), a monochromator and a magnetic lens.

The samples, reduced to powder beforehand, were placed under vacuum for 48 to 72 hours and then analysed.

Imaging of the Cuticle by Two-Photon Fluorescence Microscopy

Multiphoton microscopy on DISCO apparatus (Synchrotron Soleil).

Lambda exc=810 nm, power 18%, turquoise blue and ochre filter 406/15 (SHG), blue filter 460/60, green filter 550/88.

II. Hydrolysate a) Ash

Pressing has a very significant effect on the ash content in the hydrolysate obtained, whatever insect is studied (FIG. 8). In fact, the decrease in the ash content can reach 52%, and the proportional decrease is fairly similar whether the insects are naturally rich in minerals or not. Thus, in the case of *H. illucens* the ash content changes from 7.5 g/100 g of dry matter when the method with grinding is used, to 3.8 g/100 g of dry matter when a pressing step is added, i.e. 49% decrease; in the case of *T. molitor*, it changes from 5 g/100 g to 2.4 g/100 g, i.e. 52% decrease.

Figure 9:
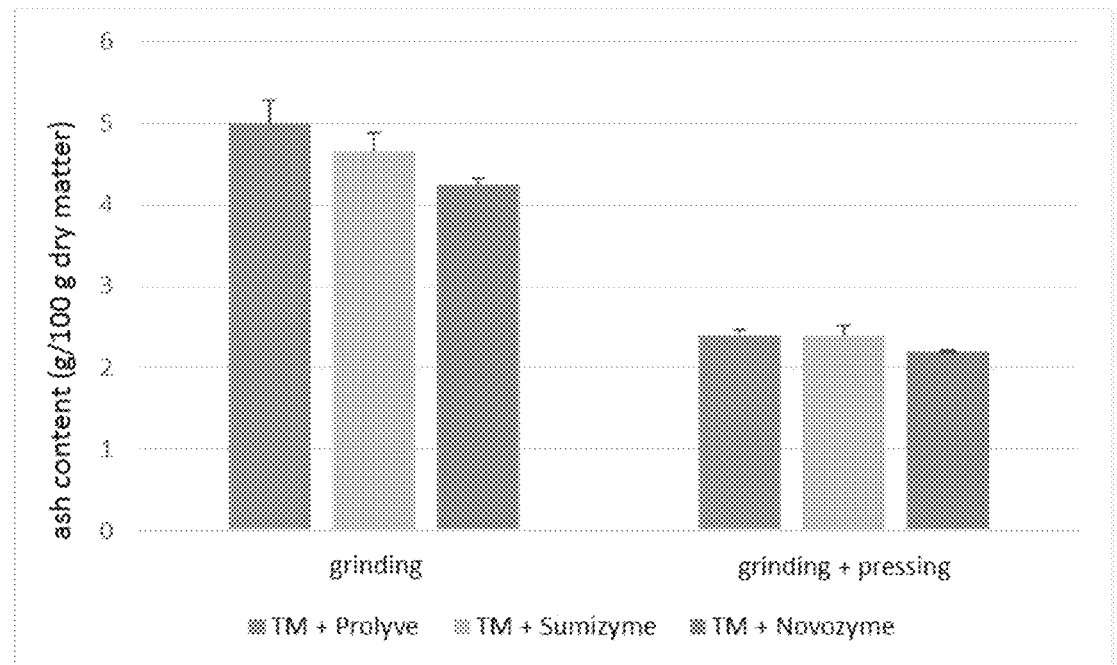

Pressing also has a significant effect on the ash content in the hydrolysate obtained, whatever enzyme is used (FIG. 9). In particular, it is noted that for *T. molitor*, regardless of the enzyme, the ash content in the hydrolysate is less than 3% when the method with pressing is used.

Figure 10:
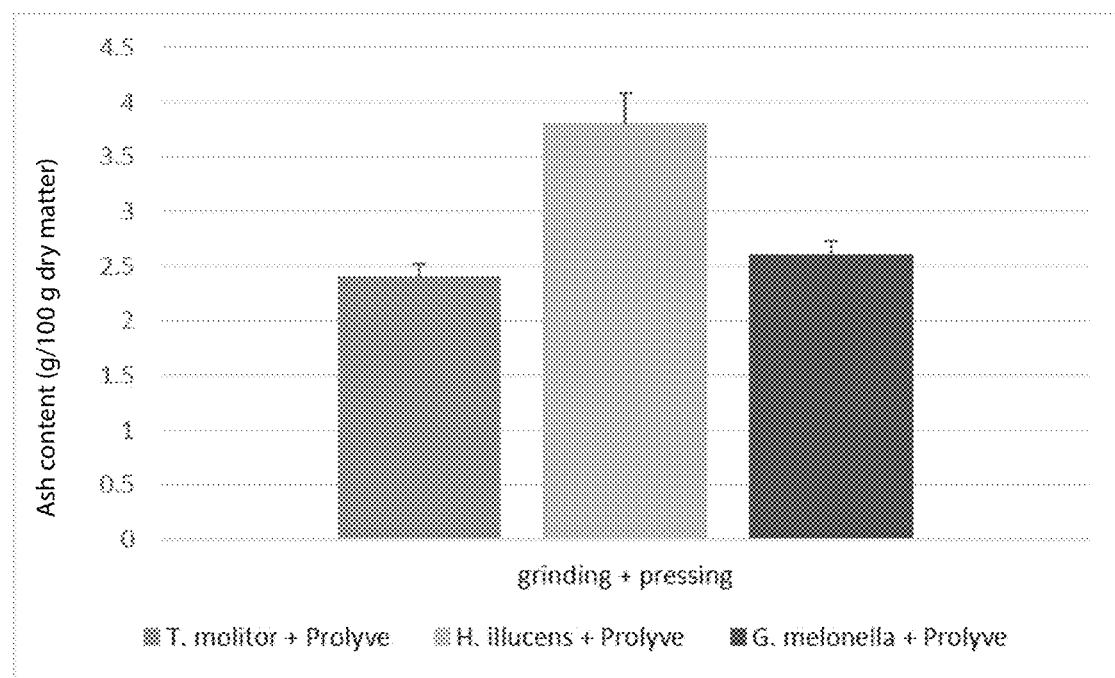
Figure 11:
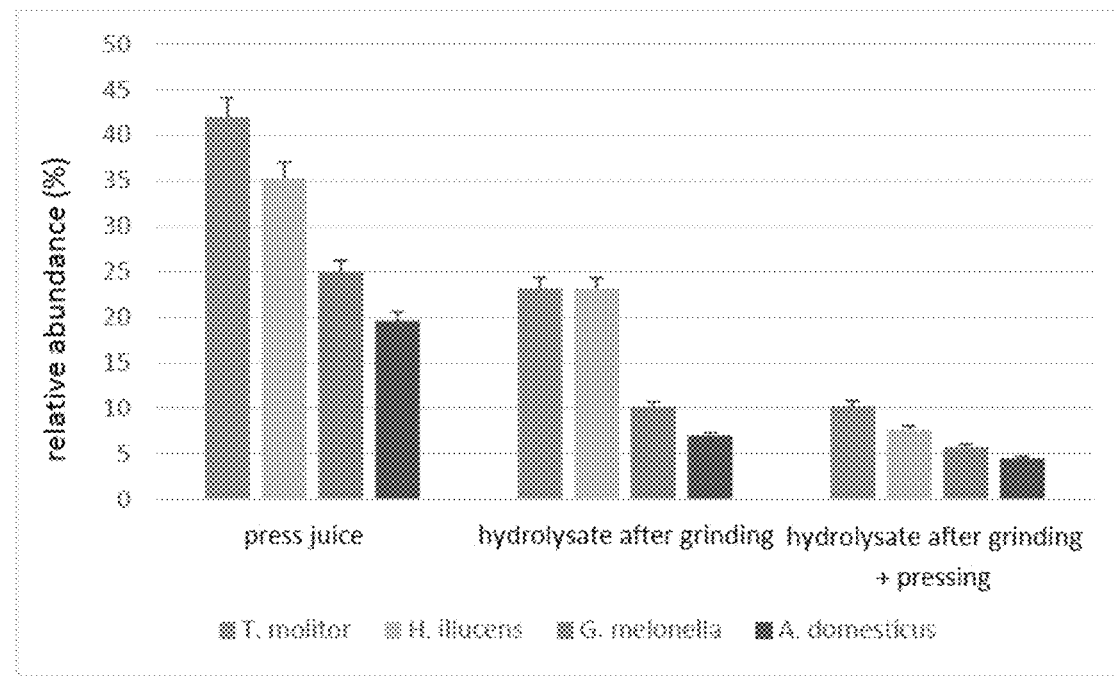

The ash content in the hydrolysate (obtained by the grinding+pressing method) is less than 4 g/100 g of dry matter, whatever insect is studied (FIG. 10).

b) Size of the Proteins in the Hydrolysate

Figure 12:
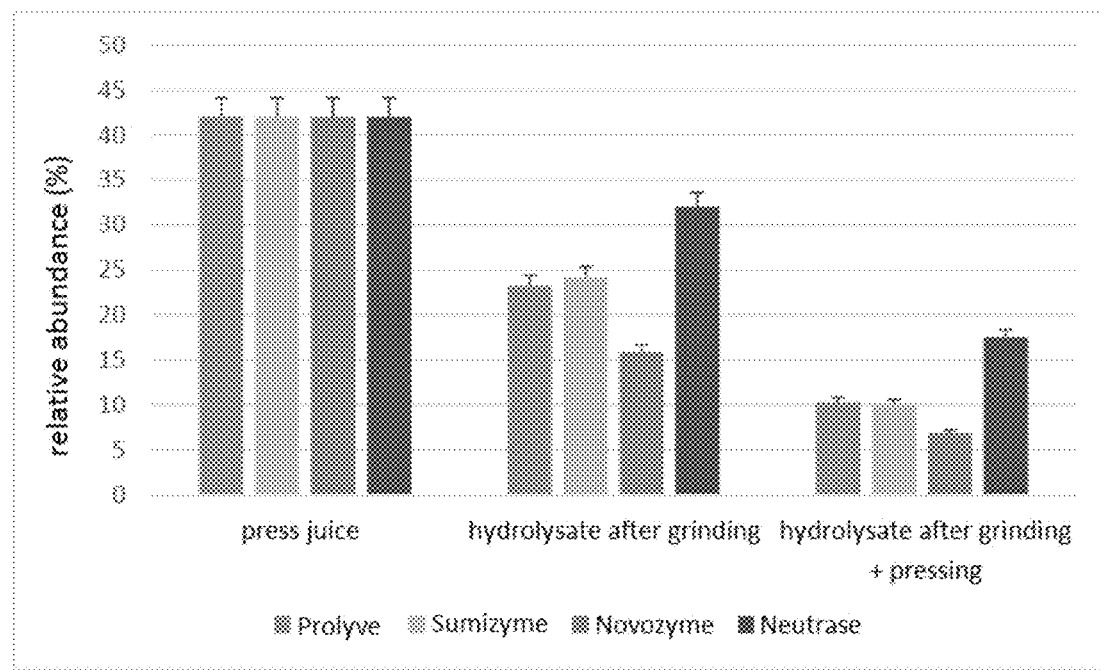

Use of the pressing step clearly makes it possible to improve the performance of the proteolytic enzymes, whatever insect (FIG. 11) or enzyme is used (FIG. 12). The relative abundance of large proteins thus drops significantly relative to the method only comprising the grinding step, the final hydrolysate not comprising more than max. 10.3% thereof in the case of hydrolysis carried out with Prolyve, whatever the insect; and not more than 17.5% in the case of hydrolysis of *T. molitor*, whatever enzyme is used.

c) Protein Content

Figure 13:
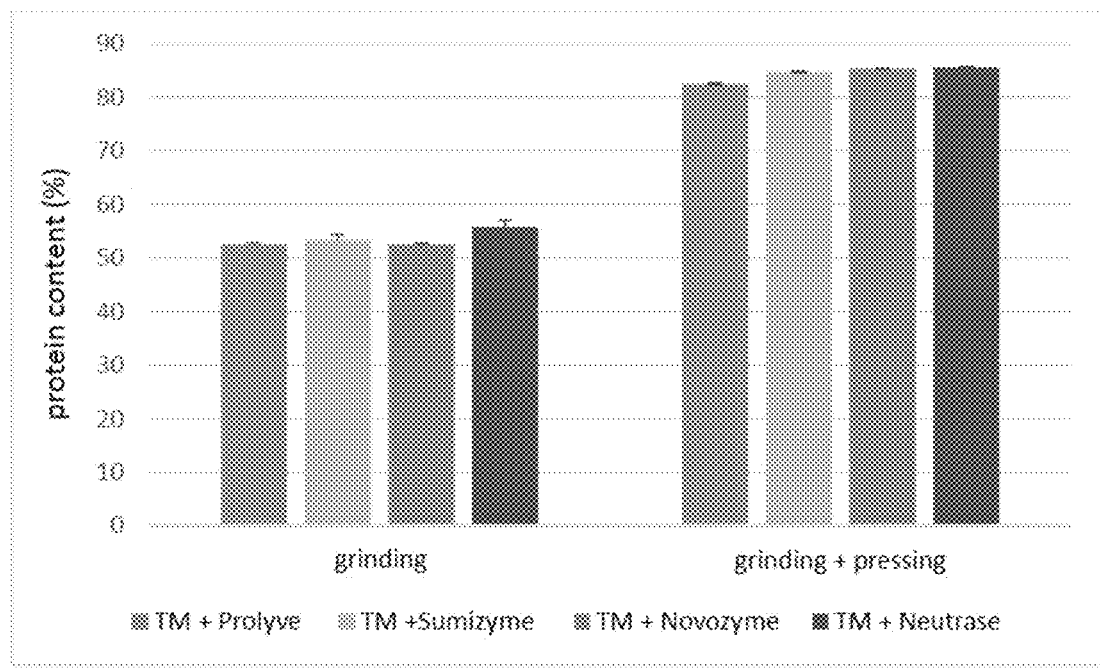

The protein content of the hydrolysate is highly dependent on the method used. Thus, when grinding is applied alone, proteins only represent 53.59±1.5% of the dry matter of the hydrolysate from *T. molitor* thus obtained, whatever enzyme is used (FIG. 13). However, when grinding is followed by pressing, the protein content in the hydrolysate becomes 84.58±1.4%, it thus undergoes an increase of 53-62%, depending on the enzyme used.

Figure 14:
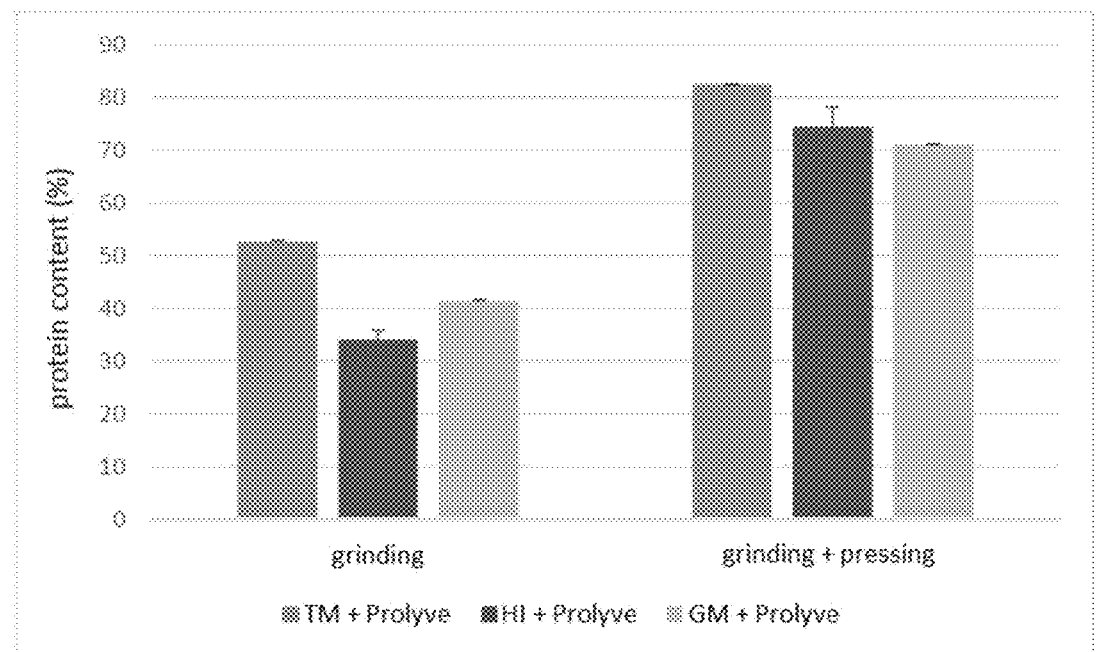
Figure 15:
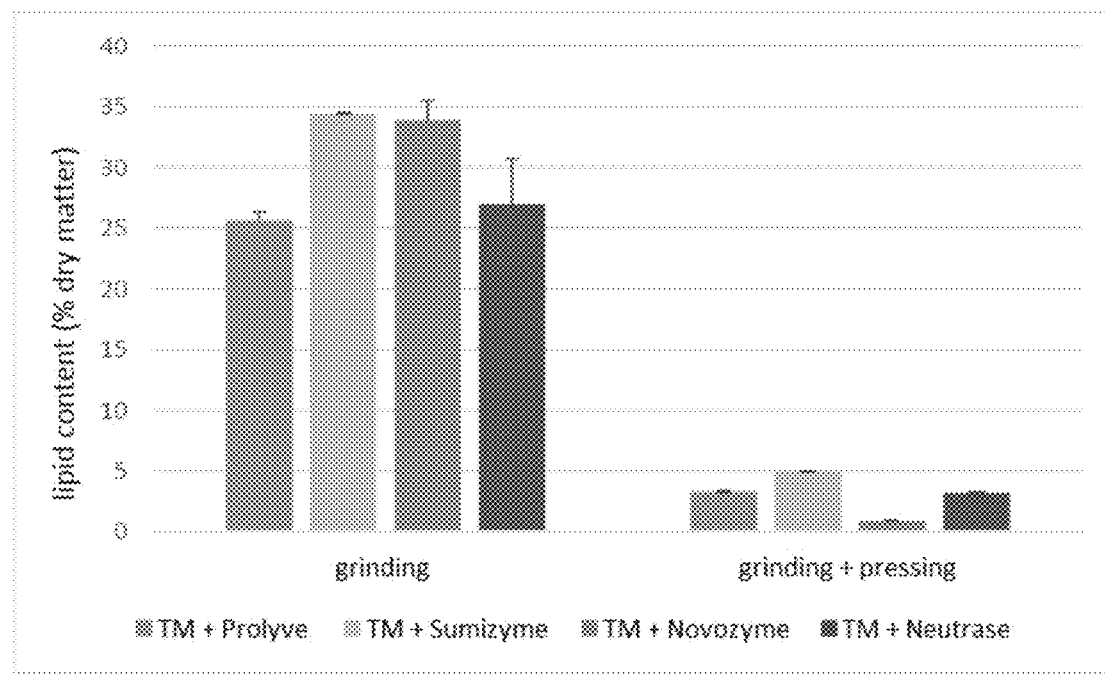

This increase is greater if the insect was initially poor in proteins, thus in the case of *G. melonella*, the protein content changes from 41.25% to 71%, experiencing an increase of nearly 86%, and in the case of *H. illucens* the increase is even 118%, since it changes from 34.2% to 74.5% (FIG. 14).

d) Lipid Content

Figure 16:
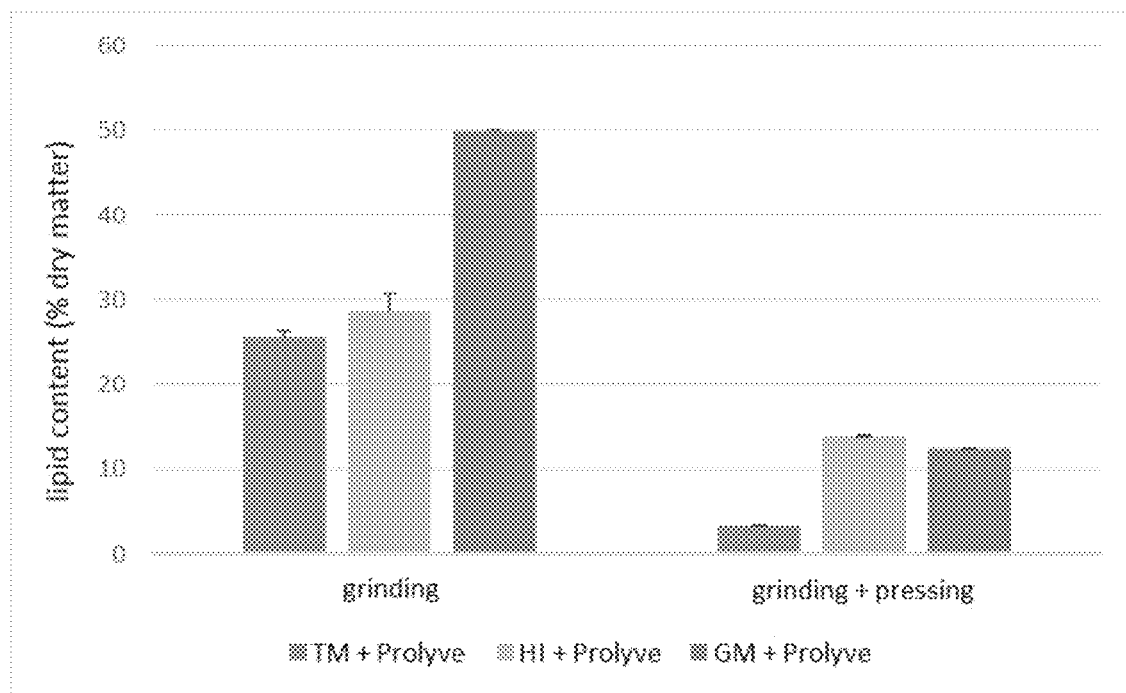

Pressing has a major influence on the lipid content of the hydrolysate, whatever enzyme (FIG. 15) or insect is studied (FIG. 16). In fact, the lipid content decreases drastically by 51.4-97.7%, thus changing from 28.6 to 13.9% in the case of *H. illucens* (51.4% decrease) and from 33.85 to 0.9% in the case of *T. molitor* with Novozyme (97.3% decrease).

e) Pepsin Digestibility

Figure 17:
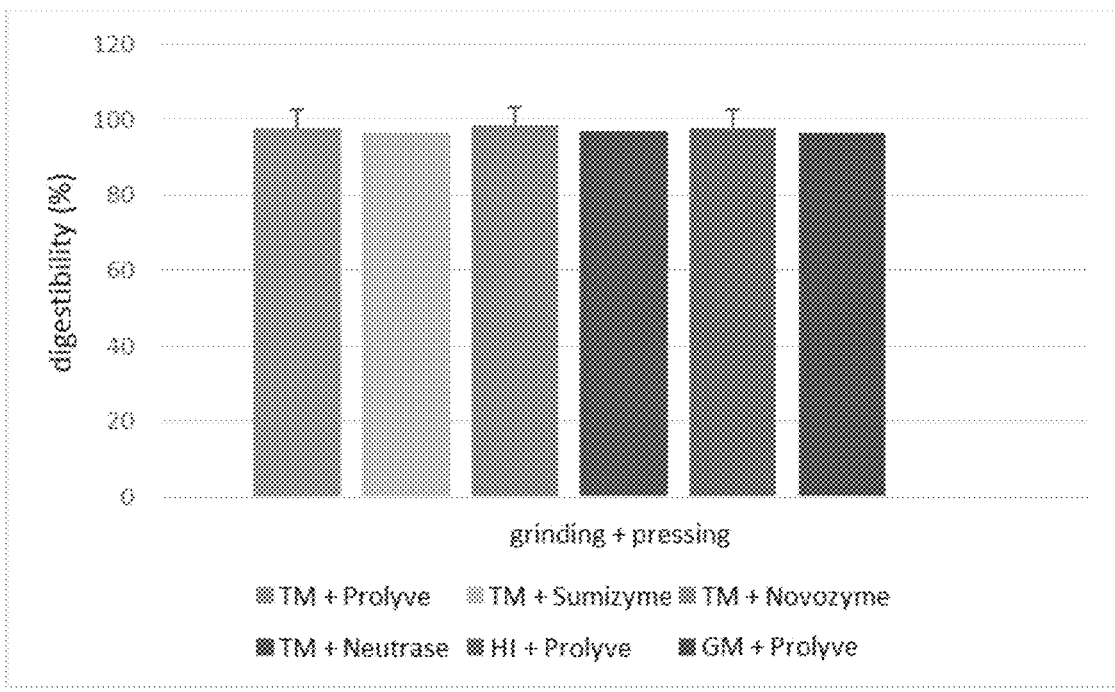

The pepsin digestibility of the hydrolysates thus obtained is very high, greater than 96%, whatever enzyme or insect is studied (FIG. 17).

f) Amino Acid Abundance

Use of the pressing step makes it possible to obtain better extraction of the other amino acids present in the cuticle, such as alanine and tyrosine and, to a lesser extent, valine, serine and glycine, whatever enzyme or insect is studied (FIGS. 18-24). These results should also be compared with those relating to the amino acids present in the enzymatically purified chitin (FIG. 29-35).

Note:

although the relative abundance of certain amino acids, including aspartic acid and glutamate in particular, decreases, their quantities remain identical, or even increase slightly in certain cases, since the total quantity of amino acids extracted by the method with a pressing step increases (cf. protein content in the hydrolysate).

III. Chitin a) Ash

Figure 25:
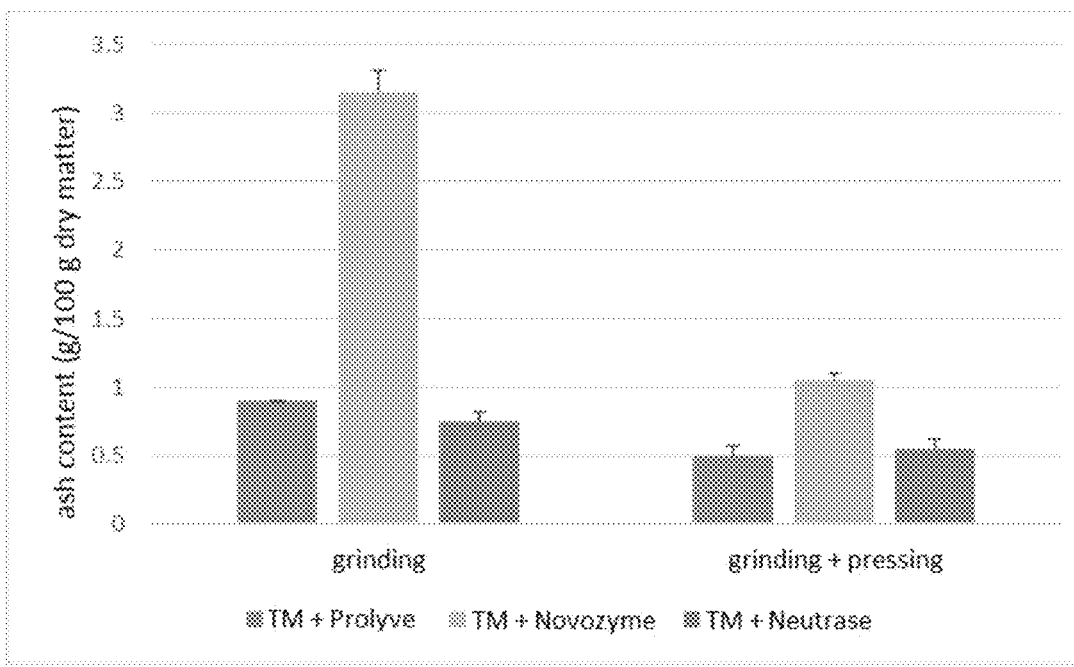
Figure 26:
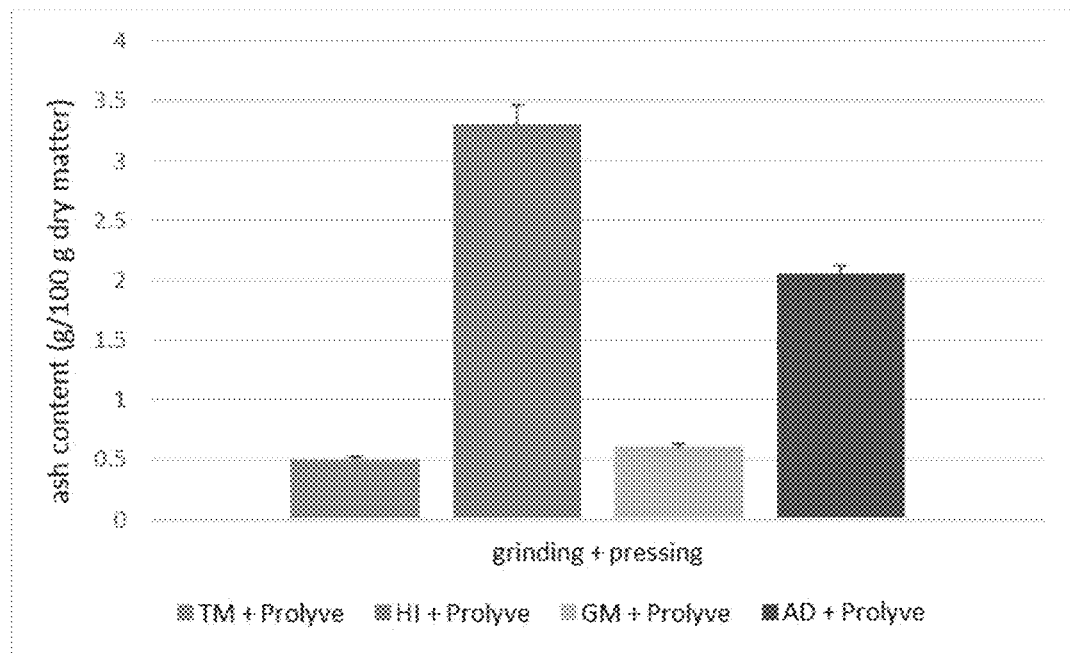

The ash content in chitin is also affected by the pressing step, although to a lesser degree than for the hydrolysate. A decrease ranging from 25% to 28.6% as a function of the enzyme used is thus observed (FIG. 25).

The ash content in chitin (obtained by the grinding+pressing method) is extremely low, whatever insect (FIG. 26) is studied. Thus, in the case of *T. molitor*, the maximum ash content is 1.05 g/100 g of dry matter, and even for insects naturally rich in minerals it remains less than 3.5 g/100 g of dry matter.

b) Lipid Content in Chitin

Figure 27:
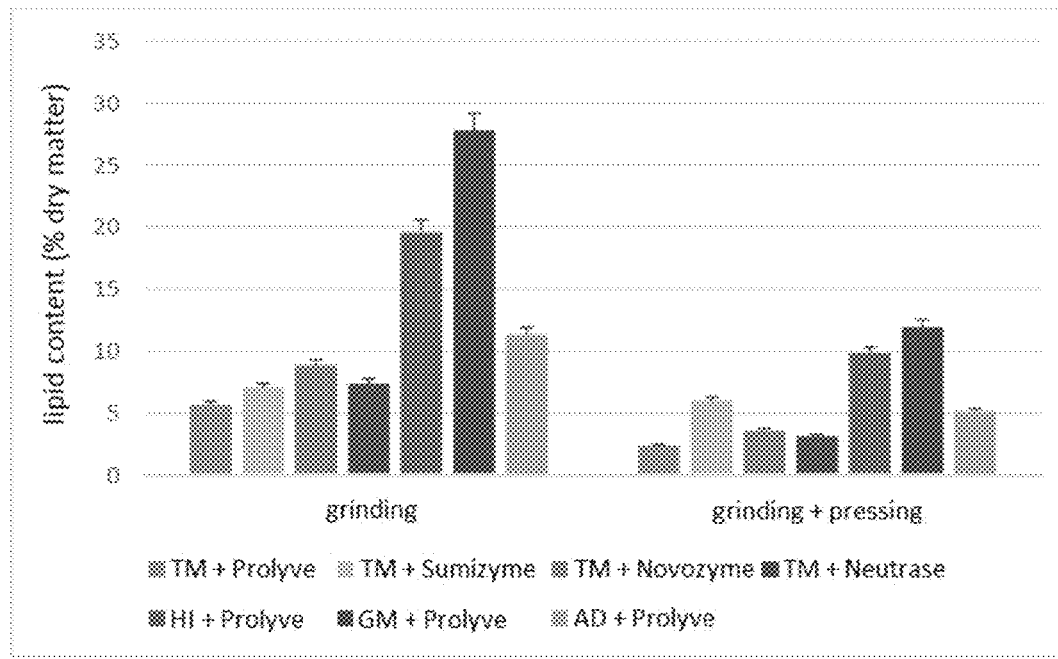

Although to a slightly lesser extent than for the hydrolysate, the lipid content in the chitin also decreases when the pressing step is added to the method (FIG. 27). The efficiency depends essentially on the enzyme, from 15% for Sumizyme and up to 60% for Novozyme. Whatever the insect, this decrease is situated between 50% in the case of *H. illucens* and 58% in the case of *T. molitor*, when the reaction is carried out with Prolyve.

For all the insects, the lipid content is less than 12%, and for the non-flying insects it is even ≤6%.

c) Content and Relative Abundance of Amino Acids in Chitin

Figure 28:
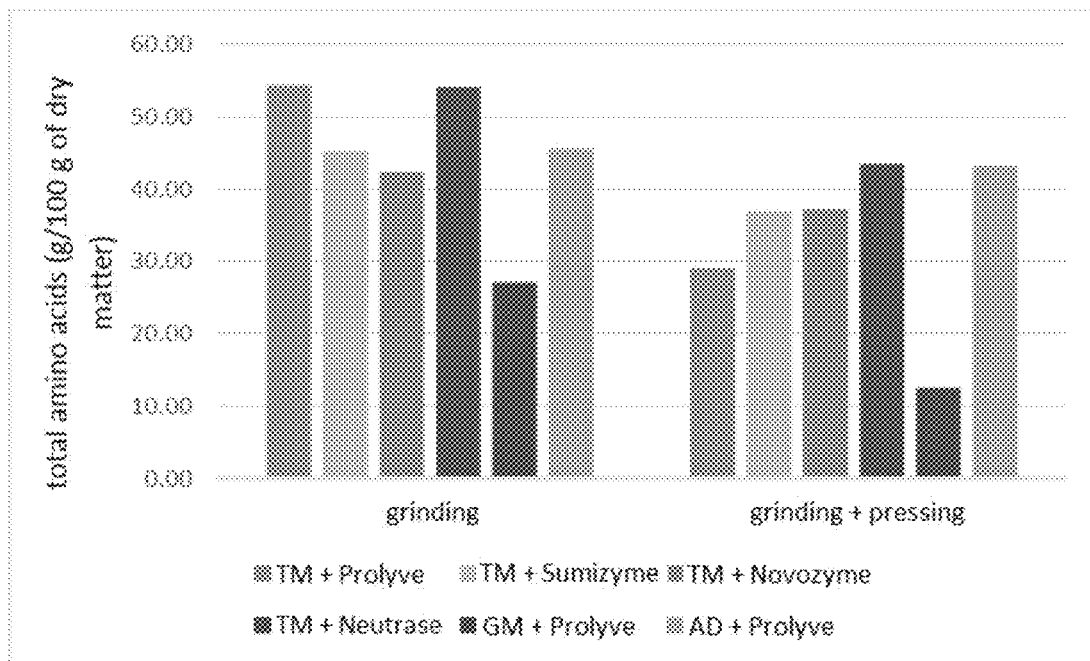

The pressing step makes it possible to eliminate a greater proportion of the proteins attached to chitin. As direct measurement of the protein content is made difficult owing to the amide function present in the actual structure of chitin, this protein content was approximated by the sum of the amino acids (FIG. 28). Thus, it can be seen that the sum of the amino acids decreases, by 5 to 54%, when the pressing step is added to the method, whatever enzyme or insect is studied.

The relative abundance of the amino acids is little affected by the pressing step, although some amino acids, including alanine, seem to be extracted better when the pressing step is carried out (FIGS. 29 to 35). Nevertheless, it can be said that for all the insects, alanine, tyrosine and proline, as well as to a lesser extent valine, glycine, leucine and serine, are amino acids mainly attached to chitin, their content is comprised on average between 23 and 40% of all the amino acids, and it is also among these amino acids that the largest decreases are seen in the chitin and the largest increases (reaching a maximum of 7-30%) in the hydrolysate (FIGS. 18-24) when a pressing step is added to the method.

d) Gravimetric Purity

Regardless of what enzyme (FIG. 36) or insect (FIG. 37) is studied, the gravimetric purity is improved by using the pressing step. Thus, it changes from 48.7% to 77.1% in the case of *T. molitor* with Prolyve and from 33.7% to 87.9% in the case of *H. illucens* with Prolyve.

e) Colorimetric Purity

Figure 38:
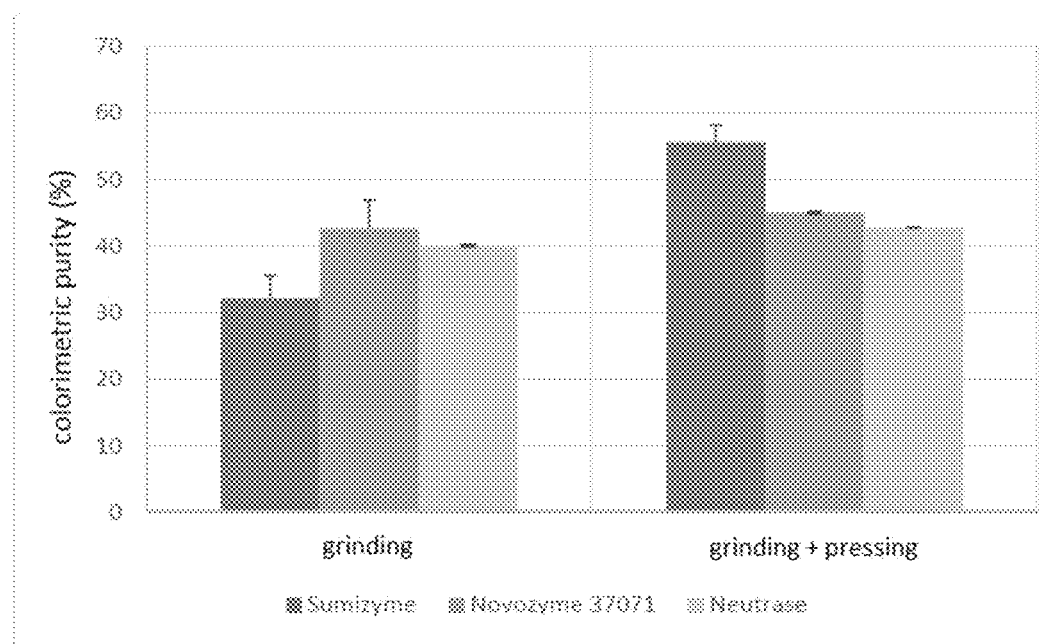
Figure 39:
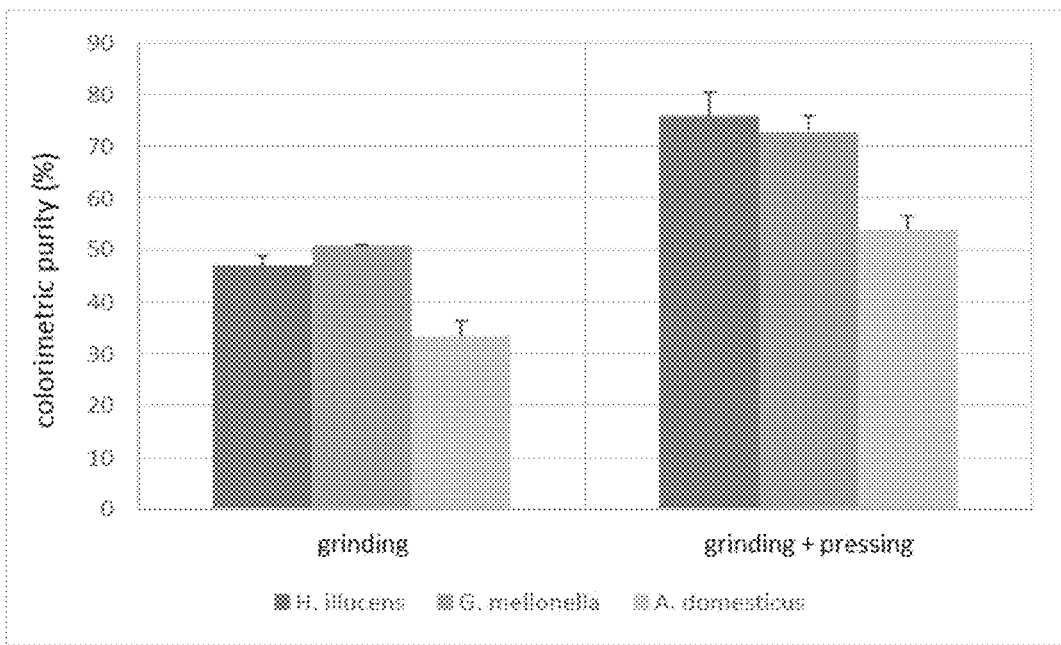

An improvement in the colorimetric purity, admittedly less marked than for the gravimetric purity, is also observed when the pressing step forms part of the method, whatever enzyme or insect is studied (FIGS. 38 and 39).

f) Purity by Difference

Figure 40:
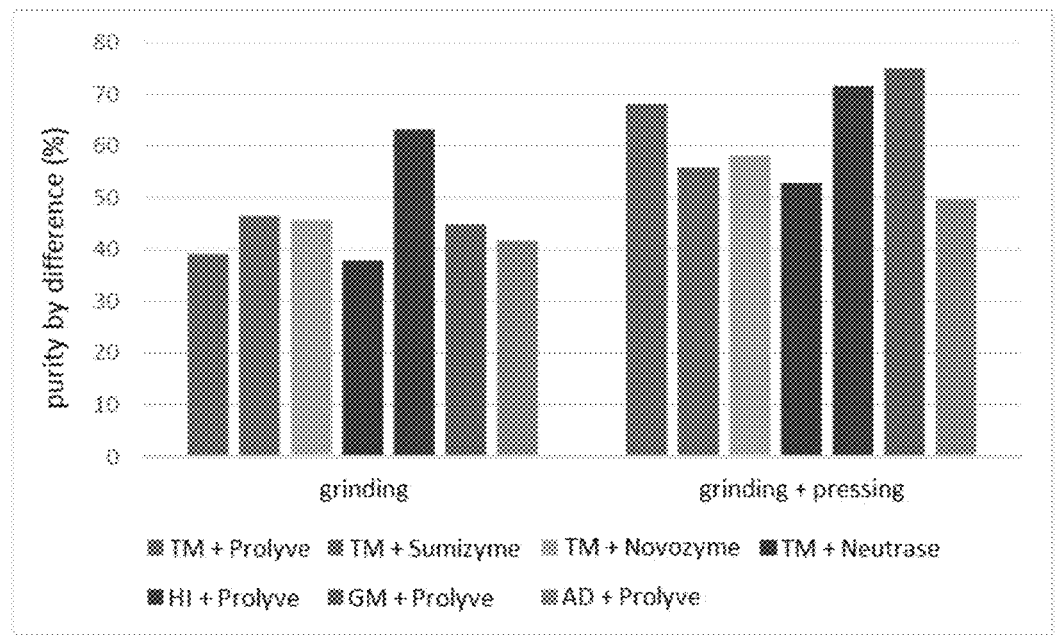

Owing to the decrease in the lipid, ash and amino acids content in the chitin obtained after the method with pressing, the purity by difference for this chitin increases significantly, by 13% in the case of *H. illucens* and up to 74% in the case of *T. molitor* with Prolyve, whatever insect or enzyme is studied (FIG. 40).

g) Degree of Acetylation of Chitin

Figure 41:
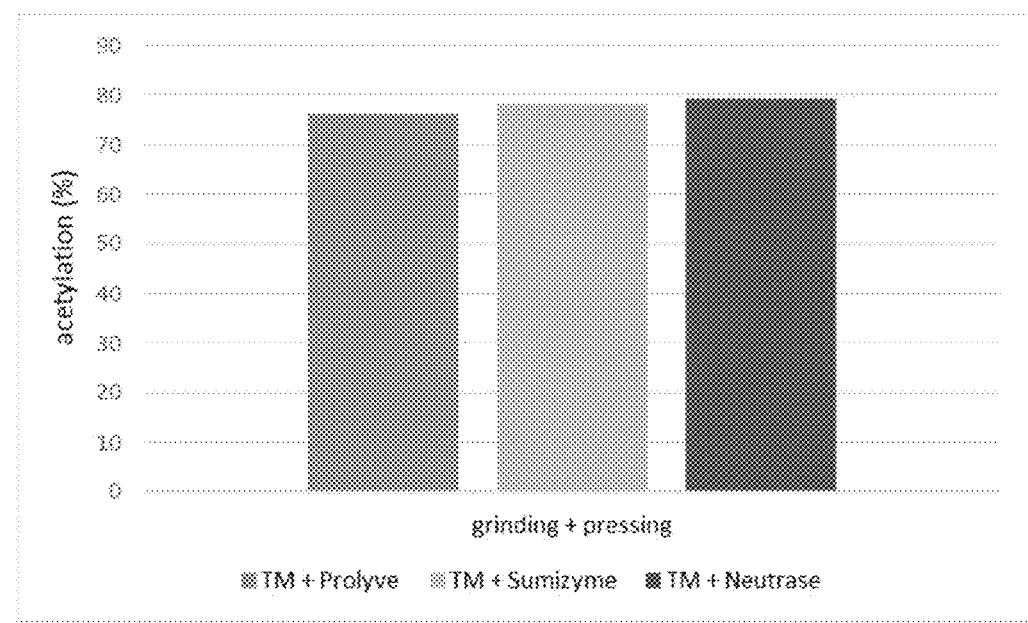
Figure 42:
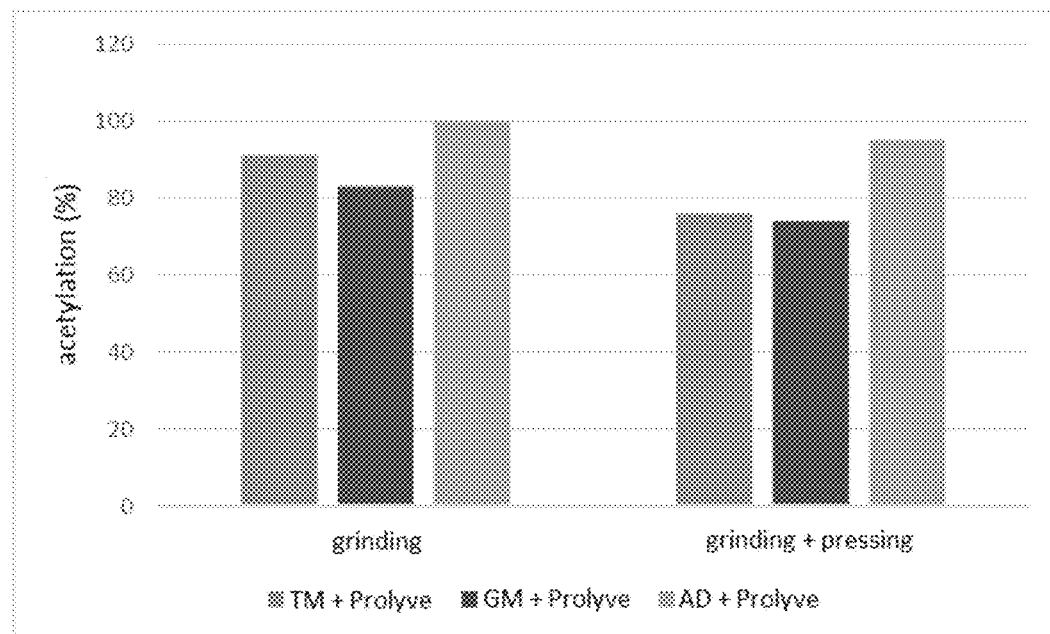

The degree of acetylation is significantly affected by adding the pressing step to the method (FIGS. 41 and 42). In fact, removal of the lipids and amino acids from the haemolymph allows greater accessibility of the enzymes to the surface of the cuticle, which contributes to an improvement in cleavage of the peptide bonds of the proteins bound to the chitin, but also, through catalytic promiscuity, cleavage of the amide bonds of the chitin. Thus, the degree of acetylation of the chitin of *T. molitor* resulting from the method is comprised between 76 and 79%, whereas in the absence of the pressing step, it is 91% and even chemical hydrolysis, carried out under severe conditions of temperature and reagents, leads to a degree of acetylation of 85%.

For the other insects considered, in particular *G. melonella* and *A. domesticus*, the degree of acetylation is also affected by the method, thus it changes from 83 to 74% in one case and from 100 to 95% in the other case, respectively.

As the solubility and processability of chitin are quite particularly linked to its degree of acetylation, this concomittant hydrolysis of the amide bond of the N-acetylglucosamine units of chitin is an unexpected positive effect of enzymatic hydrolysis carried out under these conditions.

h) Atomic and Functional Surface Abundances

As purification proceeds, the distribution of the atoms on the surface of the chitin shows an increase in the relative oxygen content and a decrease in the relative carbon content (Table 4).

Moreover, the bonds of the carbon atoms on the surface tend to pass from bonds predominantly of the hydrocarbon type (C—H, C—C), to bonds of the alcohol type (C—O) or carbonyl type (C═O). There is also a decrease in bonds of the amide type (N—C═O).

However, what seems to be the most representative is the alcohol bond/hydrocarbon bond ratio (C—O/C—H), and in the context of enzymatically purified chitin this ratio is comprised between 0.31 and 0.56, but more specifically between 0.39 and 0.41.

In Table 4:
- by "raw cuticle" is meant the chitin of the cuticle in the native state, analysed directly after extraction from the insect by dissection;
- by "enzymatically purified chitin (Novozyme)" is meant a chitin resulting from a method comprising grinding+pressing and enzymatic hydrolysis in the presence of the enzyme Novozyme 37071;
- by "enzymatically purified chitin (Prolyve)" is meant a chitin resulting from a method comprising grinding+pressing and enzymatic hydrolysis in the presence of the enzyme Prolyve NP;
- by "enzymatically purified chitin" is meant a chitin resulting from a method comprising grinding+pressing and enzymatic hydrolysis in the presence of the enzyme Prolyve;
- by "pure chitin" is meant a chitin obtained by chemical purification, identical to that used for determining the quantity of chitin in the insect

TABLE 4

Distribution of certain atoms and bonds on the surface of chitin

| | | atoms | | types of bonds | | | | ratio |
|---|---|---|---|---|---|---|---|---|
| | | C | O | C—H | C—O | C═O | N—C═O | (C—O)/(C—H) |
| TM | raw cuticle | 78.85 | 16.23 | 68.88 | 20.16 | 6.87 | 3.53 | 0.29 |
| | enzymatically purified chitin (Novozyme) | 75.71 | 18.50 | 62.88 | 24.21 | 9.93 | 2.98 | 0.39 |
| | enzymatically purified chitin (Prolyve) | 75.64 | 19.40 | 57.54 | 29.57 | 10.67 | 2.22 | 0.51 |
| | pure chitin | 64.24 | 30.31 | 39.5 | 42.36 | 16.21 | 1.92 | 1.07 |
| AD | enzymatically purified chitin | 78.49 | 16.37 | 68.16 | 20.84 | 8.48 | 2.32 | 0.31 |
| | pure chitin | 67.27 | 27.30 | 42.32 | 40.46 | 13.59 | 3.63 | 0.96 |
| GM | enzymatically purified chitin | 76.24 | 19.29 | 63.15 | 25.15 | 8.9 | 2.81 | 0.40 |
| | pure chitin | 64.93 | 28.87 | 34.1 | 45.39 | 18.07 | 2.44 | 1.33 |
| HI | raw cuticle | 86.09 | 12.69 | 83.35 | 8.41 | 2.55 | 5.68 | 0.10 |
| | enzymatically purified chitin | 74.46 | 21.10 | 61.49 | 25.07 | 7.95 | 5.49 | 0.41 |
| | pure chitin | 73.10 | 22.49 | 53 | 30.3 | 11.16 | 4.11 | 0.57 | i) Imaging of the Cuticle by Two-Photon Fluorescence Microscopy

Figure 43:
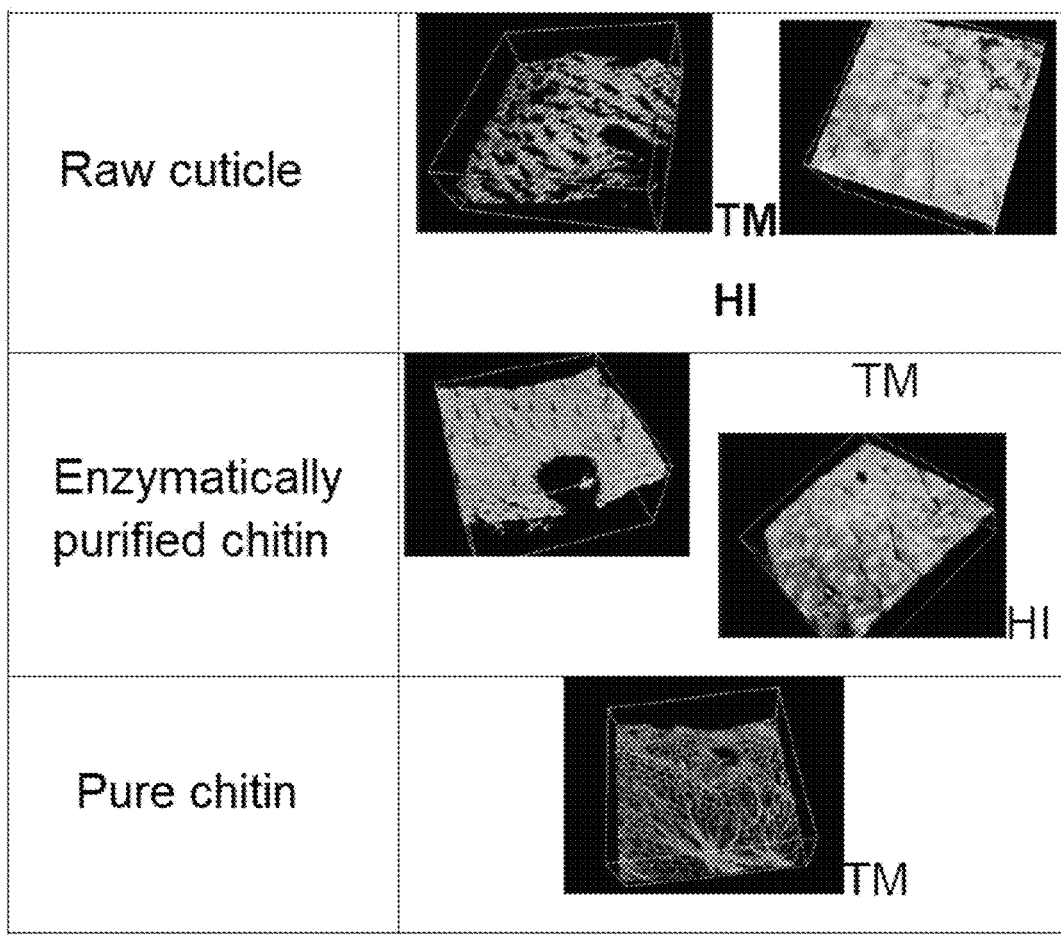
Figure 44:
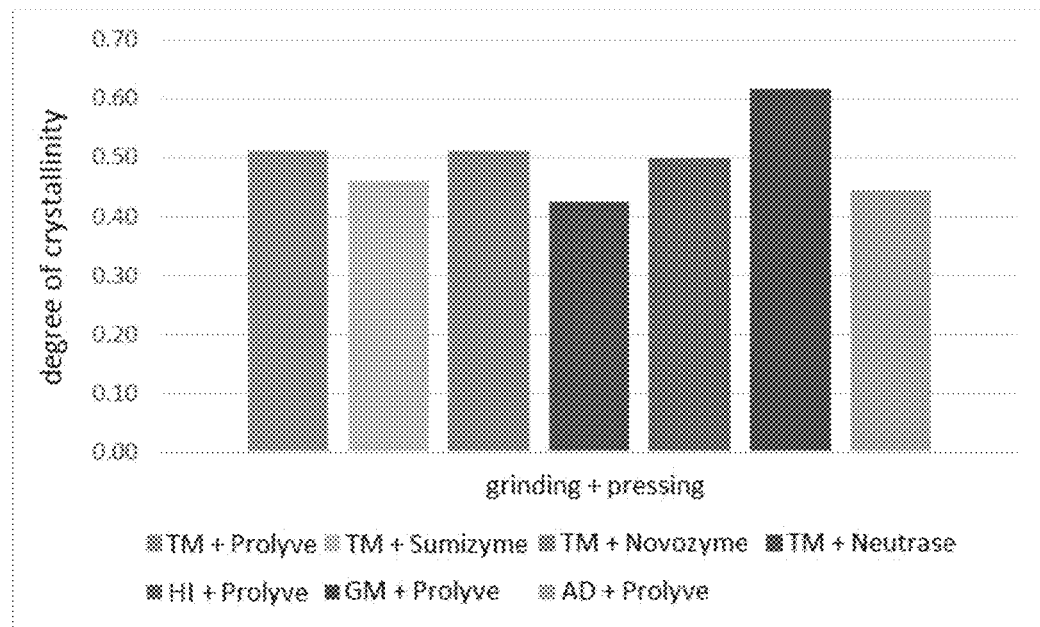

The partial purification of chitin by the enzymatic route by the method according to the invention makes it possible to maintain the flexibility of the whole by preserving protein "filling" of the chitin structures, compared to chemical purification, while removing the protein overload on the exterior of the structure (see FIG. 43).

The terminology used in FIG. 43 is the same as that defined in section III h) above.

j) Degree of Crystallinity

Whatever insect or enzyme is studied, the degree of crystallinity, i.e. the ratio of the crystalline and amorphous areas, of the chitin obtained is comprised between 0.42 and 0.61.

Generally, the term crystallinity index is used in the literature, i.e. the ratio of the peak heights (and not of the areas). This measurement carries a substantial risk of error. Nevertheless, for purposes of comparison, the crystallinity index of the samples was also measured, and it is situated between 88 and 95% for all of the insects, and is even greater than 90% for the Coleoptera and the Lepidoptera.

EXAMPLE 6: METHOD ACCORDING TO THE INVENTION WITH RECOVERY OF THE PROTEIN FRACTION ORIGINATING FROM THE PRESS JUICE

I. Material and Methods
a) Material
Insect
The following insect was studied:
a coleopteron: *Tenebrio molitor* (*T. molitor* or TM).
Enzyme
Prolyve was used in the hydrolysis.

| enzyme | Prolyve |
|---|---|
| Desired enzymatic activity | 3789.52 |

-continued

| enzyme | Prolyve |
|---|---|
| Enzymatic activity/g | 3789.52 |
| m (g) | 1.00 | b) Methods of Production

Method of Production with Grinding Followed by Pressing (Designated "Grinding+Pressing" in the Figures)

Several batches were transformed as follows: 600 g of fresh *T. molitor* larvae are introduced into a chamber, where they are killed with steam (115° C., 5 minutes). The insects are then introduced into a mixer and 75 mL of water is added per 100 g of insects, and the whole is then mixed and pressed (twin-screw press, or filter press, or other pressing system).

The press cake is then dried at 70° C. overnight. The press juice, on the other hand, is centrifuged for 30 minutes with a force of 3000 g and the solid part is recovered—insoluble proteins of the haemolymph.

125 g of press cake and 125 g (wet weight, approximately 30% by weight dry) of insoluble haemolymph proteins are then introduced into a three-necked flask equipped with a condenser and a magnetic stirrer, 1250 mL of water is added as well as a proteolytic enzyme with an activity equivalent to 9500 SAPU. The reaction is then heated at 45° C. for 4 hours. The temperature is then raised to 90° C. for 15 minutes, and the reaction mixture is finally filtered (0.40-0.45 μm). The residue is dried for 24 hours at 70° C.: this is therefore chitin obtained by purification by the enzymatic route; the filtrate is frozen and lyophilized: this is therefore the hydrolysate.

c) Analyses

Measurement of the ash content, measurement of the lipid content, the relative abundance of amino acids and measurement of the size of the proteins were carried out as in Example 5.

II. Characterization of the Products Obtained

Figure 45:
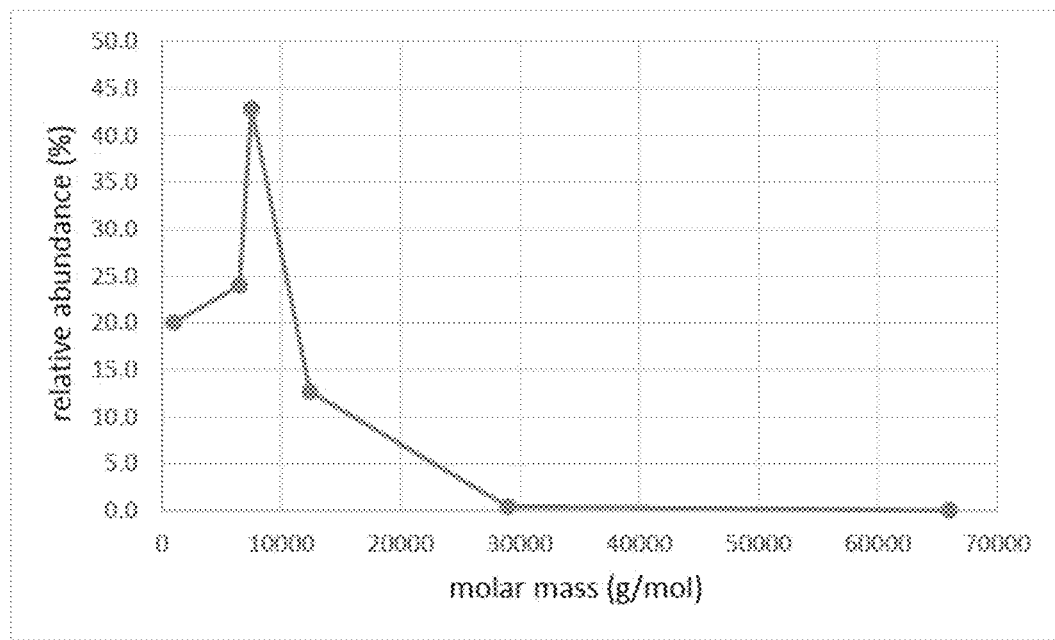

The products obtained, the chitin and the hydrolysate, were analysed and characterized (Table 5, FIG. 45).

TABLE 5

Characterization

| | Hydrolysate | Chitin |
|---|---|---|
| Ash | 4.1 | 0.5 |
| Lipids | 12.85 | 3.7 |
| Digestibility | 95 | n.a. |
| Amino acids (relative abundance, %) | | |
| Asp | 9.7 | 5.4 |
| Glu | 12.8 | 6.7 |
| Ala | 9.0 | 13.7 |
| Arg | 2.5 | 3.6 |
| Cys | 1.1 | 0.5 |
| Gly | 5.9 | 9.4 |
| His | 3.3 | 3.9 |
| Ile | 5.4 | 4.8 |
| Leu | 8.5 | 8.0 |
| Lys | 6.5 | 2.9 |
| Met | 1.5 | 0.4 |
| Phe | 4.0 | 2.6 |
| Pro | 6.9 | 8.3 |
| Ser | 4.4 | 5.8 |
| Thr | 4.9 | 3.5 |
| Tyr | 4.7 | 11.3 |
| Val | 7.7 | 9.0 |
| Trp | 1.3 | 0.6 | n.a.: not applicable

The invention claimed is:

1. A method for the production of chitin and/or chitosan and/or an hydrolysate from insects, comprising the following steps:
    (i) grinding insect cuticles into particles such that at the end of grinding, the size of the particles is between 500 μm and 0.5 cm, and then
    (ii) pressing the insect cuticles to obtain a press cake comprising an oil content less than or equal to 12%, and then
    (iii) enzymatically hydrolyzing the press cake with a proteolytic enzyme, wherein said pressing removes a press juice comprising fat and wherein no second grinding step is performed.

2. The method according to claim 1, further comprising a step of killing the insects prior to the grinding step.

3. The method according to claim 1, further comprising a step of treating the insect cuticles with an oxidizing agent prior to enzymatic hydrolysis.

4. The method according to claim 1, in which the insects are selected from the group consisting of the Coleoptera, the Lepidoptera, the Orthoptera, and the Diptera.

5. The method according to claim 1, in which the proteolytic enzyme is a protease selected from the group consisting of aminopeptidases, metallocarboxypeptidases, serine endopeptidases, cysteine endopeptidases, aspartic endopeptidases, and metalloendopeptidases.

6. The method according to claim 3, wherein chitin and/or chitosan is/are produced.

7. The method according to claim 3, wherein an hydrolysate is produced.

8. A method for the production of chitin from cuticles of insects, comprising the following steps in the following order:
    a) killing the insects,
    b) grinding the insects into particles such that at the end of grinding, the size of the particles is between 500 μm and 0.5 cm,
    c) pressing the insects to obtain a press cake comprising an oil content less than or equal to 12%,
    d) enzymatically hydrolyzing the press cake with a proteolytic enzyme, and
    e) recovering the chitin,
wherein said pressing removes a press juice comprising fat and wherein no second grinding step is performed.

9. A method for the production of an hydrolysate from insects, comprising the following steps:
    a) killing the insects,
    b) grinding the insects into particles such that at the end of grinding, the size of the particles is between 500 μm and 0.5 cm,
    c) pressing the insects to obtain a press cake comprising an oil content less than or equal to 12%,
    d) enzymatically hydrolyzing the press cake with a proteolytic enzyme, and
    e) recovering the hydrolysate,
wherein said pressing removes a press juice comprising fat and wherein no second grinding step is performed.

10. A method for the production of chitosan from insect cuticles, comprising the following steps:
    a) killing the insects,
    b) grinding the insects into particles such that at the end of grinding, the size of the particles is between 500 μm and 0.5 cm,
    c) pressing the insects to obtain a press cake comprising an oil content less than or equal to 12%,
    d) enzymatically hydrolyzing the insect cuticlespress cake with a protease,
    e) recovering the chitin,
    f) deacetylating the recovered chitin recoveredto produce chitosan, and
    g) recovering the chitosan,
wherein said pressing removes a press juice comprising fat and wherein no second grinding step is performed.

* * * * *